United States Patent [19]
Shinjo et al.

[11] Patent Number: 5,328,640
[45] Date of Patent: Jul. 12, 1994

[54] FERROELECTRIC CHIRAL SMECTIC LIQUID CRYSTAL COMPOSITION AND LIQUID CRYSTAL DEVICE USING SAME

[75] Inventors: Kenji Shinjo, Atsugi; Takao Takiguchi, Tokyo; Hiroyuki Kitayama, Sagamihara; Kazuharu Katagiri, Tokyo; Masahiro Terada, Atsugi; Takeshi Togano, Yokohama; Masataka Yamashita, Hiratsuka; Takashi Iwaki, Isehara; Shosei Mori, Atsugi, all of Japan

[73] Assignee: Canon Kabushiki Kaisha, Tokyo, Japan

[21] Appl. No.: 40,392

[22] Filed: Mar. 30, 1993

Related U.S. Application Data

[63] Continuation of Ser. No. 370,985, Jun. 23, 1989, abandoned.

[30] Foreign Application Priority Data

| Jun. 24, 1988 | [JP] | Japan | 63-157675 |
| Jul. 13, 1988 | [JP] | Japan | 63-175784 |
| Jun. 9, 1989 | [JP] | Japan | 1-147993 |

[51] Int. Cl.$^5$ .................... C09K 19/34; G02F 1/13
[52] U.S. Cl. ...................... 252/299.61; 359/106
[58] Field of Search ............ 252/299.61; 359/106

[56] References Cited

U.S. PATENT DOCUMENTS

| 4,708,441 | 11/1987 | Petrzilka et al. | 350/346 |
| 4,826,621 | 5/1989 | Terashima et al. | 252/299.61 |
| 4,834,904 | 5/1989 | Krause et al. | 252/299.01 |
| 4,892,393 | 1/1990 | Terashima et al. | 359/103 X |
| 4,911,863 | 3/1990 | Sage et al. | 252/299.65 |

FOREIGN PATENT DOCUMENTS

| 0178647 | 4/1986 | European Pat. Off. |
| 0191860 | 8/1986 | European Pat. Off. |
| 0237007 | 9/1987 | European Pat. Off. |
| 0255962 | 2/1988 | European Pat. Off. |
| 0267585 | 5/1988 | European Pat. Off. |
| 0267758 | 5/1988 | European Pat. Off. |
| 0278665 | 8/1988 | European Pat. Off. |
| 0335348 | 10/1989 | European Pat. Off. |
| WO8606373 | 11/1986 | World Int. Prop. O. |

Primary Examiner—Richard D. Lovering
Assistant Examiner—C. Harris
Attorney, Agent, or Firm—Fitzpatrick, Cella, Harper & Scinto

[57] ABSTRACT

A ferroelectric chiral smectic liquid crystal composition, comprising at least one compound represented by the following formula (I):

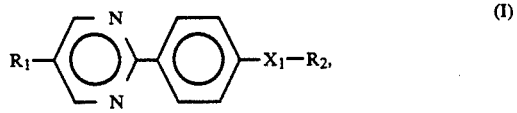

wherein $R_1$ and $R_2$ respectively denote a linear or branched alkyl group having 1–18 carbon atoms capable of having a substituent, at least one of $R_1$ and $R_2$ being optically active; and $X_1$ denotes a single bond, —O—,

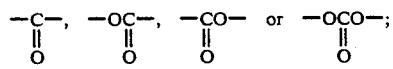

and at least one compound represented by the following formula (II):

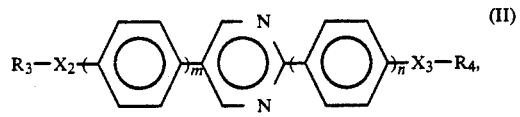

wherein $R_3$ and $R_4$ respectively denote a linear or branched alkyl group having 1–18 carbon atoms capable of having a substituent; $X_2$ and $X_3$ respectively denote a single bond, —O—,

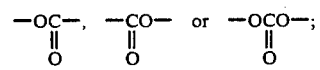

and m and n are respectively 0, 1 or 2 with proviso that $m+n=2$ or more.

7 Claims, 7 Drawing Sheets

FERROELECTRIC CHIRAL SMECTIC LIQUID CRYSTAL COMPOSITION AND LIQUID CRYSTAL DEVICE USING SAME

This application is a continuation of application Ser. No. 370,985, filed Jun. 23, 1989, now abandoned.

FIELD OF THE INVENTION AND RELATED ART

The present invention relates to a liquid crystal composition used in a liquid crystal display device, a liquid crystal-optical shutter, etc., more particularly to a novel liquid crystal composition with improved responsiveness to an electric field and a liquid crystal device using the liquid crystal composition.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127-128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4367924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected.

A simple matrix display apparatus including a device comprising such a ferroelectric liquid crystal layer between a pair of substrates may be driven according to a driving method as disclosed in, e.g., Japanese Laid-Open Patent Applications Nos. 193426/1984, 193427/1984, 156046/1985 and 156047/1985.

FIGS. 4A and 4B are waveform diagrams showing driving voltage waveforms adopted in driving a ferroelectric liquid crystal panel as an embodiment of the liquid crystal device according to the present invention. FIG. 5 is a plan view of such a ferroelectric liquid crystal panel 51 having a matrix electrode structure. Referring to FIG. 5, the panel 51 comprises scanning lines 52 and data lines 53 intersecting with the scanning lines. Each intersection comprises a ferroelectric liquid crystal disposed between a scanning line 52 and a data line 53 to form a pixel.

Referring to FIG. 4A, at $S_S$ is shown a selection scanning signal waveform applied to a selected scanning line, at $S_N$ is shown a non-selection scanning signal waveform applied to a non-selected scanning line, at $I_S$ is shown a selection data signal waveform (providing a black display state) applied to a selected data line, and at $I_N$ is shown a non-selection data signal waveform applied to a non-selected data line. Further, at $I_S$-$S_S$ and $I_N$-$S_S$ in the figure are shown voltage waveforms applied to pixels on a selected scanning line, whereby a pixel supplied with the voltage $I_S$-$S_S$ assumes a black display state and a pixel supplied with the voltage $I_N$-$S_S$ assumes a white display state. FIG. 4B shows a time-serial waveform used for providing a display state as shown in FIG. 6.

In the driving embodiment shown in FIGS. 4A and 4B, a minimum duration $\Delta t$ of a single polarity voltage applied to a pixel on a selected scanning line corresponds to the period of a writing phase $t_2$, and the period of a one-line clearing phase $t_1$ is set to $2\Delta t$.

The parameters $V_S$, $V_I$ and $\Delta t$ in the driving waveforms shown in FIGS. 4A and 4B are determined depending on switching characteristics of a ferroelectric liquid crystal material used.

FIG. 7 shows a V-T characteristic, i.e., a change in transmittance T when a driving voltage denoted by $(V_S+V_I)$ is changed while a bias ratio as mentioned hereinbelow is kept constant. In this embodiment, the parameters are fixed at constant values of $\Delta t=50$ $\mu$s and a bias ratio $V_I/(V_I+V_S)=\frac{1}{3}$. On the right side of FIG. 7 is shown a result when the voltage $(I_N$-$S_S)$ shown in FIG. 4 is applied to a pixel concerned, and on the left side of FIG. 7 is shown a result when the voltage $(I_S$-$S_S)$ is applied to a pixel concerned, respectively while increasing the voltage $(V_S+V_I)$. On both sides of the ordinate, the absolute value of the voltage $(V_S+V_I)$ is separately indicated. Herein, a voltage $V_1$ denotes the absolute value of $(V_S+V_I)$ required for switching from a white state to a black state by applying a voltage signal $V_B{}^2$ shown in FIG. 4A, a voltage $V_2$ denotes the absolute value of $(V_S+V_I)$ required for switching (re-setting) a black state to a white state by applying a voltage $V_R$ at $I_N$-$S_S$, and a voltage $V_1$ is the value of $(V_S+V_I)$ beyond which a pixel concerned written in white is unexpectedly inverted into a black state. In this instance, a relationship of $V_2<V_1<V_3$ holds. The voltage $V_1$ may be referred to as a threshold voltage in actual drive and the voltage $V_3$ may be referred to as a crosstalk voltage. Such a crosstalk voltage $V_3$ is generally present in actual matrix drive of a ferroelectric liquid crystal device. In an actual drive, $\Delta V=(V_3-V_1)$ provides a range of $|V_S+V_I|$ allowing a matrix drive and may be referred to as a (driving) voltage margin, which is preferably large enough. It is of course possible to increase the value of $V_3$ and thus $\Delta V$ $(=V_3-V_1)$ by increasing the bias ratio (i.e., by causing the bias ratio to approach a unity). However, a large bias ratio corresponds to a large amplitude of a data signal and leads to an increase in flickering and a lower contrast, thus being undesirable in respect of image quality. According to our study, a bias ratio of about $\frac{1}{4}-\frac{1}{3}$ was practical. On the other hand, when the bias ratio is fixed, the voltage margin $\Delta V$ strongly depends on the switching characteristics of a liquid crystal material used, and it is needless to say that a liquid crystal material providing a large $\Delta V$ is very advantageous for matrix drive.

The upper and lower limits of application voltages and a difference therebetween (driving voltage margin $\Delta V$) by which selected pixels are written in two states of "black" and "white" and non-selected pixels can retain the written "black" and "white" states at a constant temperature as described above, vary depending on and are inherent to a particular liquid crystal material used. Further, the driving margin is deviated according to a change in environmental temperature, so that optimum driving voltages should be set in an actual display apparatus according to a liquid crystal material used and an environmental temperature.

In a practical use, however, when the display area of a matrix display apparatus is enlarged, the differences in environmental conditions (such as temperature and cell gap between opposite electrodes) naturally increase, so that it becomes impossible to obtain a good quality of image over the entire display area by using a liquid crystal material having a small driving voltage margin.

On the other hand, it is known that the ferroelectric liquid crystal molecules under such nonhelical conditions are disposed in succession so that their directors (longer molecular axes) are gradually twisted between the substrates and do not show a uniaxial orientation or alignment (i.e., in a splay alignment state). A problem in this case is a low transmittance through the liquid crystal layer.

Transmitted light intensity I through a liquid crystal is given by the following equation with respect to the incident light intensity $I_0$ under cross nicols when the uniaxial alignment of the molecules is assumed:

$$I=I_0 \sin^2(4\theta a)\cdot\sin^2(\pi\Delta nd/\lambda) \qquad (1),$$

wherein $\Delta n$ denotes the refractive index anisotropy of the FLC; d, the cell thickness; $\lambda$, the wavelength of the incident light; and $\theta a$, a half of the angle between two stable states (tilt angle).

When a conventional FLC cell is used, it has been experimentally known that $\theta a$ is 5–8 degrees under a twisted alignment condition. The control of physical properties affecting the term $\Delta nd\pi/\lambda$ cannot be easily performed, so that it is desired to increase $\theta a$ to increase I. However, this has not been successfully accomplished by only a static alignment technique.

With respect to such a problem, it has been proposed to utilize a torque relating to a dielectric anisotropy $\Delta\epsilon$ of an FLC (1983 SID report from AT & T; Japanese Laid-Open Patent Applns. 245142/1986, 246722/1986, 246723/1986, 246724/1986, 249024/1986 and 249025/1986). More specifically, a liquid crystal molecule having a negative $\Delta\epsilon$ tends to become parallel to the substrates under application of an electric field. By utilizing this property, if an effective value of AC electric field is applied even in a period other than switching, the above-mentioned twisted alignment is removed, so that $\theta a$ is increased to provide an increased transmittance (AC stabilization effect). A torque $\Gamma P_S$ acting on FLC molecules involved in switching of states and a torque $\Gamma\Delta\epsilon$ acting on FLC molecules relating to the AC stabilization effect are respectively proportional to physical properties as shown in the following formulas:

$$\Gamma P_S \propto P_S \cdot E \qquad (2)$$

$$\Gamma\Delta\epsilon \propto \tfrac{1}{2}\Delta\epsilon\cdot\epsilon_0\cdot E^2 \qquad (3)$$

The above formula (3) apparently shows that the sign and absolute value of $\Delta\epsilon$ of the FLC play an important role.

FIG. 8 attached hereto shows the change of $\theta a$ versus Vrms experimentally measured for 4 FLCs having different values of $\Delta\epsilon$. The measurement was conducted under application of AC rectangular pulses of 60 KHz so as to remove the influence of $P_S$. The curves (I)-(IV) correspond to the results obtained by using FLCs showing the following $\Delta\epsilon$ values $$\Delta\epsilon \approx -5.5, \qquad (I)$$

$$\Delta\epsilon \approx -3.0, \qquad (II)$$

$$\Delta\epsilon \approx -0, \qquad (III)$$

$$\Delta\epsilon \approx 1.0. \qquad (IV)$$

As is clear from the graph in FIG. 8, a larger negative value of $\Delta\epsilon$ provides a large $\theta a$ at a lower voltage and thus contributes to provision of an increased I.

The transmittances obtained by using the liquid crystals (I) and (III) were 15% for (I) and 6% for (III) (under application of rectangular AC waveforms of 60 kHz and $\pm 8$ V), thus showing a clear difference.

As is known from the above examples, the display characteristics of an SSFLC (Surface-Stabilized FLC) can be remarkably changed by controlling the properties relating to $\Delta\epsilon$ and $P_S$.

In order to provide a ferroelectric liquid crystal composition having a negatively large $\Delta\epsilon$, it is most effective to include a compound having a negative $\Delta\epsilon$ with a large absolute value. For example, it is possible to obtain a compound having a negatively large $\Delta\epsilon$ by introducing a halogen or cyano group in a shorter axis direction of a molecule or by introducing a heterocyclic skeleton in a molecule.

The magnitude of $\Delta\epsilon$ of a compound having a negative $\Delta\epsilon$ substantially varies depending on the structure thereof. Some examples of such compounds are shown below:

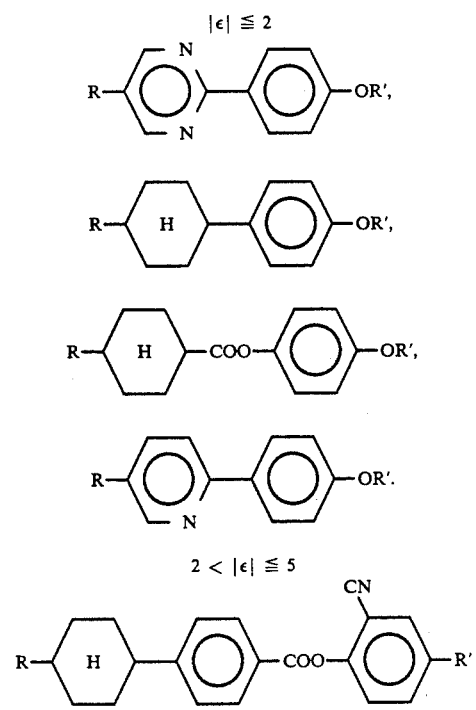

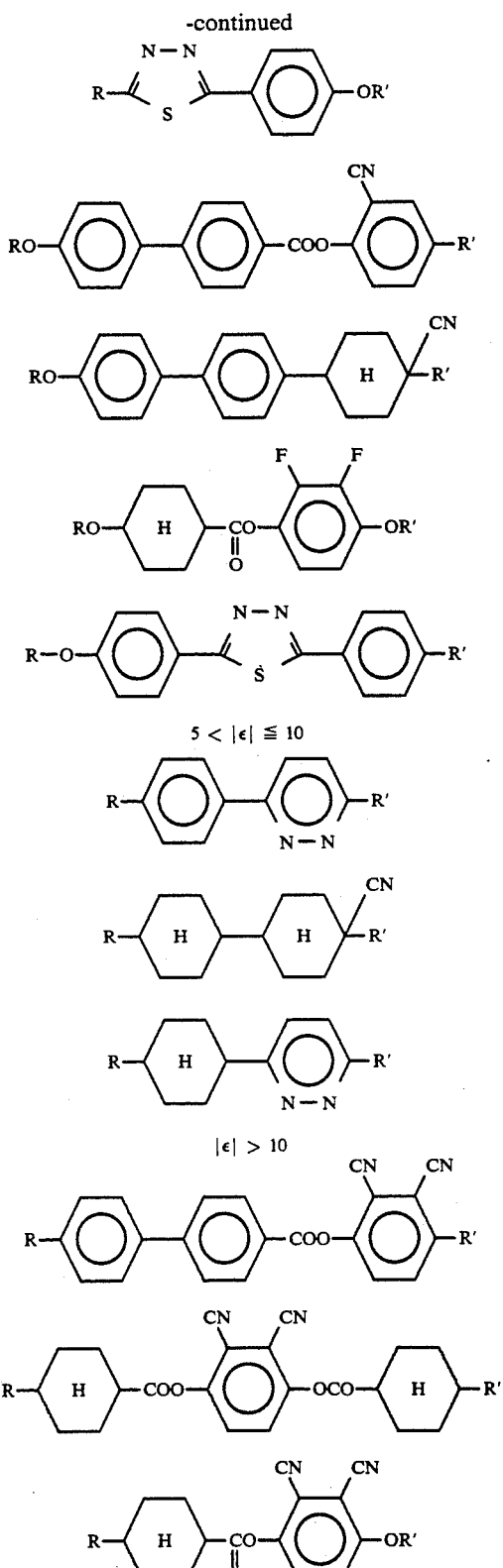

Herein, R and R' respectively denote an alkyl group. These may be classified roughly into three groups including compounds having a negatively small $\Delta\epsilon$ ($|\Delta\epsilon| \leq 2$), compounds having a negatively medium $\Delta\epsilon$ ($2 < |\Delta\epsilon| \leq 10$) and compounds having a negatively large $\Delta\epsilon$ ($|\Delta\epsilon| > 10$). Among these, compounds having a

|Δε| of ≦2 have little effect of increasing |Δε|. Compounds having a |Δε| of >10 are very effective in increasing |Δε| but those available heretofore are only dicyanohydroquinone derivatives.

However, a dicyanohydroquinone derivative, while it has a large |Δε|-increasing effect, has a high viscosity, so that it is liable to degrade a switching characteristic when its content is increased. On the other hand, among the compounds having a medium |Δε| (2<|Δε|≦10), some compounds have a moderately low viscosity while their |Δε|-increasing effect is somewhat lower than those having a large |Δε|.

From the above consideration, it is essential to select a compound having a negative anisotropy, preferably one having a |Δε| of >2, and mixing it with an appropriately selected other compound in a properly selected mixing ratio.

SUMMARY OF THE INVENTION

An object of the present invention is to provide a chiral smectic liquid crystal composition having a large driving voltage margin adapted for providing a practical ferroelectric liquid crystal device and a wide driving voltage margin affording satisfactory drive of entire pixels even when some degree of temperature fluctuation is present over a display area comprising the pixels of a liquid crystal device.

Another object of the present invention is to provide a liquid crystal composition further containing a mesomorphic compound having a negative dielectric anisotropy to show an AC stabilization effect providing remarkably improved display characteristics.

A further object of the present invention is to provide a liquid crystal device using such a liquid crystal composition and showing improved driving and display characteristics.

According to the present invention, there is provided a ferroelectric chiral smectic liquid crystal composition, comprising at least one optically active compound represented by the following formula (I):

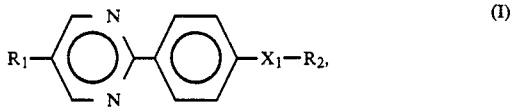

(I)

wherein $R_1$ and $R_2$ respectively denote a linear or branched alkyl group having 1-18 carbon atoms capable of having a substituent, at least one of $R_1$ and $R_2$ being optically active; and $X_1$ denotes a single bond —O—,

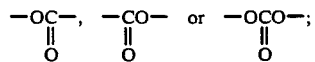

at least one compound represented by the following formula (II):

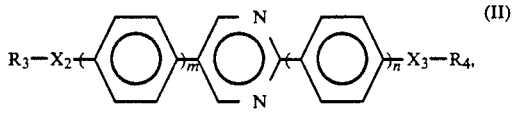

(II)

wherein $R_3$ and $R_4$ respectively denote a linear or branched alkyl group having 1-18 carbon atoms capable of having a substituent; $X_2$ and $X_3$ respectively denote a single bond, —O—, $$-\underset{\underset{O}{\|}}{O}C-, \quad -\underset{\underset{O}{\|}}{C}O- \quad or \quad -\underset{\underset{O}{\|}}{O}CO-;$$

and m and n are respectively 0, 1 or 2 with proviso that m+n=2 or more.

According to the present invention, there is further provided a ferroelectric liquid crystal composition as described above further comprising a mesomorphic compound having a negative dielectric anisotropy, which is preferably one having a Δε< −2, more preferably Δε< −5, most preferably Δε< −10.

The present invention further provides a liquid crystal device comprising a pair of substrates and such a ferroelectric liquid crystal composition as described above disposed between the electrode plates.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
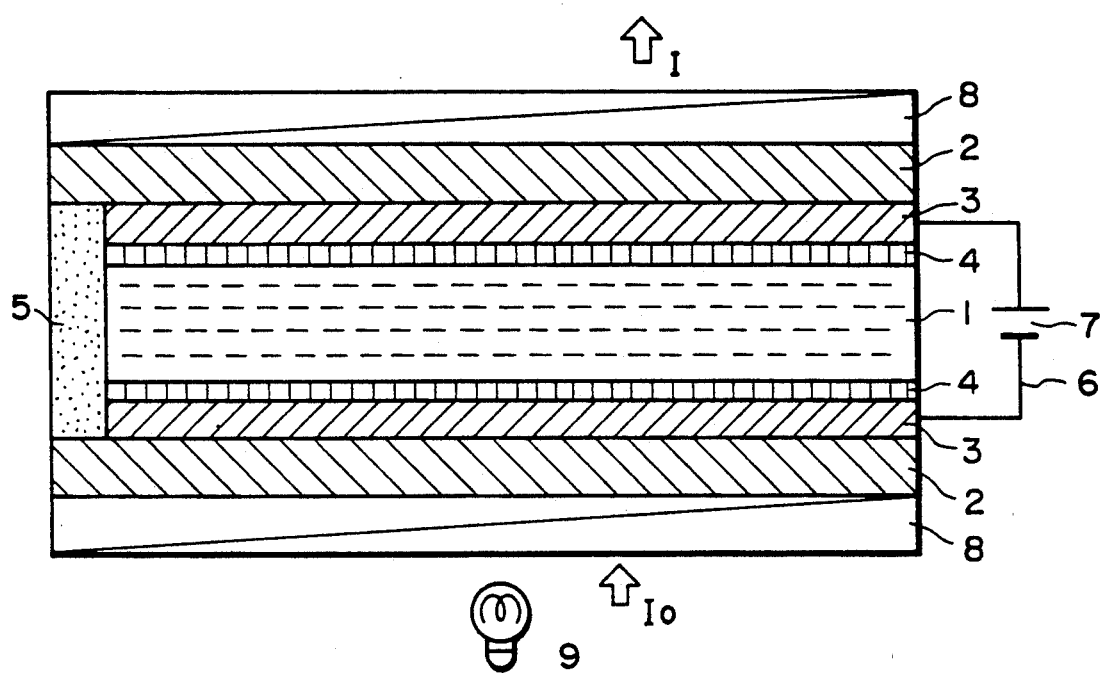
FIG. 1 is a schematic sectional view of a liquid crystal display device using a ferroelectric liquid crystal.

Preferred examples of the optically active compounds represented by the above-mentioned general formula (I) may include those represented by the following formula (I-a).

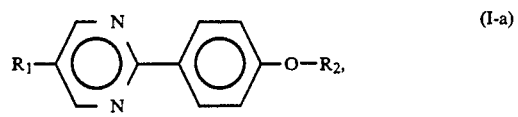

(I-a)

wherein $R_1$ and $R_2$ are the same as defined in the general formula (I).

Preferred examples of $R_1$ and $R_2$ may include those of the following (I-i) to (I-iii).

(I-i) $R_1$ is an n-alkyl group, and $R_2$ is $$+CH_2\overset{CH_3}{\underset{s}{\rightarrow}}\underset{*}{CH}-R_5,$$

wherein s is 0–7 and $R_5$ is a linear or branched alkyl group.

(I-ii) $R_1$ is $$+CH_2\overset{CH_3}{\underset{t}{\rightarrow}}\underset{*}{CH}-R_6$$

wherein t is 0–7 and $R_6$ is a linear or branched alkyl group, $R_2$ is an n-alkyl group.

(I-iii) $R_1$ is $$+CH_2\overset{CH_3}{\underset{t}{\rightarrow}}\underset{*}{CH}-R_6$$

and $R_2$ is $$+CH_2\overset{CH_3}{\underset{s}{\rightarrow}}\underset{*}{CH}-R_5,$$

wherein s and t are respectively 0–7, and $R_5$ and $R_6$ are respectively a linear or branched alkyl group.

Further, preferred examples of the compounds represented by the above-mentioned general formula (II) may include those represented by the following formulas (II-a) to (II-c).

(II-a) $R_3-X_2-$[pyrazine ring]$-$[phenyl]$-$[phenyl]$-X_3-R_4$ (II-b) $R_3-X_2-$[phenyl]$-$[pyrazine ring]$-$[phenyl]$-X_3-R_4$ (II-c) $R_3-X_2-$[phenyl]$-$[phenyl]$-$[pyrazine ring]$-X_3-R_4$ In the formulas (II-a) to (II-c), $R_3$, $R_4$, $X_2$ and $X_3$ are respectively the same as in the general formula (I). Preferred examples of $X_2$ and $X_3$ may include the following combinations (II-i) to (II-viii):

(II-i) $X_2$ is a single bond and $X_3$ is a single bond,
(II-ii) $X_2$ is a single bond and $X_3$ is —O—,
(II-iii) $X_2$ is a single bond and $X_3$ is $$-O\overset{O}{\underset{\parallel}{C}}-,$$

(II-iv) $X_2$ is a single bond and $X_3$ is $$-\overset{O}{\underset{\parallel}{C}}O-,$$

(II-v) $X_2$ is —O— and $X_3$ is a single bond,
(II-vi) $X_2$ is —O— and $X_3$ is —O—,
(II-vii) $X_2$ is —O— and $X_3$ is $$-O\overset{O}{\underset{\parallel}{C}}-,$$

(II-viii) $X_2$ is —O— and $X_3$ is $$-\overset{O}{\underset{\parallel}{C}}O-.$$

Further, preferred examples of $R_3$ and $R_4$ in the formulas (II-a) to (II-c) may include the following combinations (II-ix) to (II-xi):

(II-ix) $R_3$ is an n-alkyl group and $R_4$ is an n-alkyl group.

(II-x) $R_3$ is an n-alkyl group and $R_4$ is $$+CH_2\overset{CH_3}{\underset{p}{\rightarrow}}\underset{*}{CH}-R_7,$$

wherein p is 0–7 and $R_7$ is a linear or branched alkyl group.

(II-xi) $R_3$ is an alkyl group and $R_4$ is $$+CH_2\overset{CH_3}{\underset{q}{\rightarrow}}CH+CH_2\overset{}{\underset{r}{\rightarrow}}OR_8$$

wherein q is 0–7, r is 0 or 1 and $R_8$ is a linear or branched alkyl group.

Specific examples of the compounds represented by the above-mentioned general formula (I) may include those shown by the following structural formulas.

(1-1) $n\text{-}C_8H_{17}-$[pyrazine]$-$[phenyl]$-CH_2\underset{*}{\overset{CH_3}{C}H}C_2H_5$ (1-2) $n\text{-}C_9H_{19}-$[pyrazine]$-$[phenyl]$-CH_2\underset{*}{\overset{CH_3}{C}H}C_2H_5$ (1-3) $n\text{-}C_{11}H_{23}-$[pyrazine]$-$[phenyl]$-(CH_2)_2\underset{*}{\overset{CH_3}{C}H}C_2H_5$ (1-4) $n\text{-}C_9H_{19}-$[pyrazine]$-$[phenyl]$-O\underset{*}{\overset{CH_3}{C}H}C_6H_{13}$ (1-5) $n\text{-}C_{11}H_{23}-$[pyrazine]$-$[phenyl]$-OCH_2\underset{*}{\overset{CH_3}{C}H}C_2H_5$

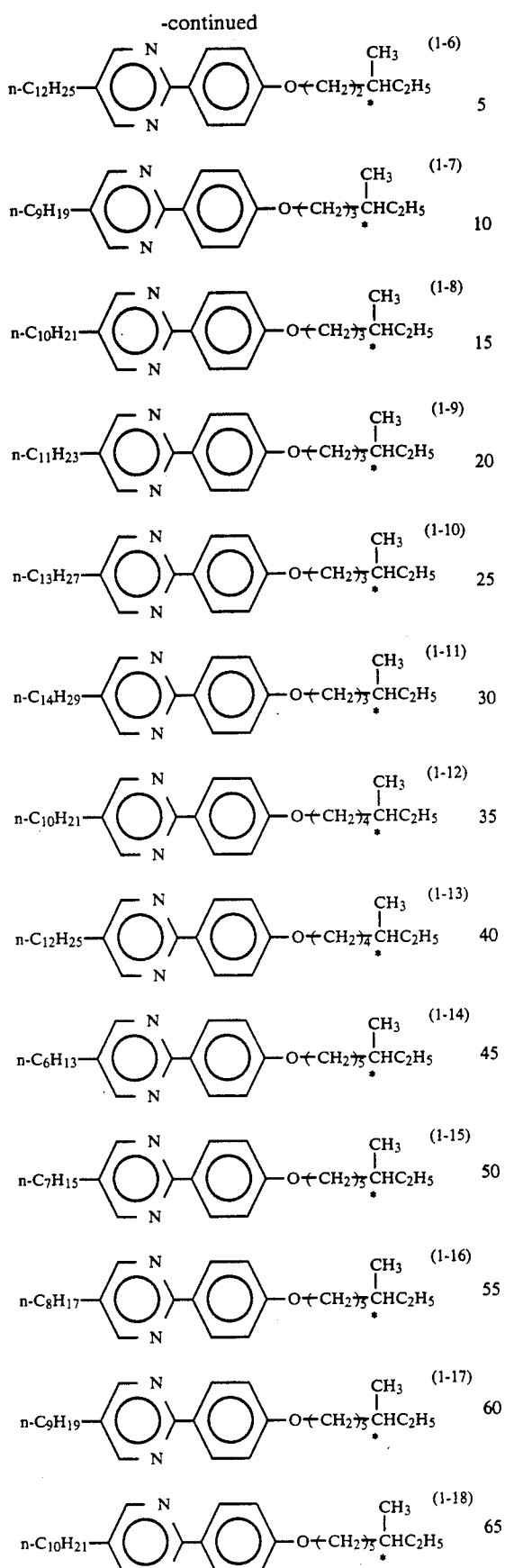
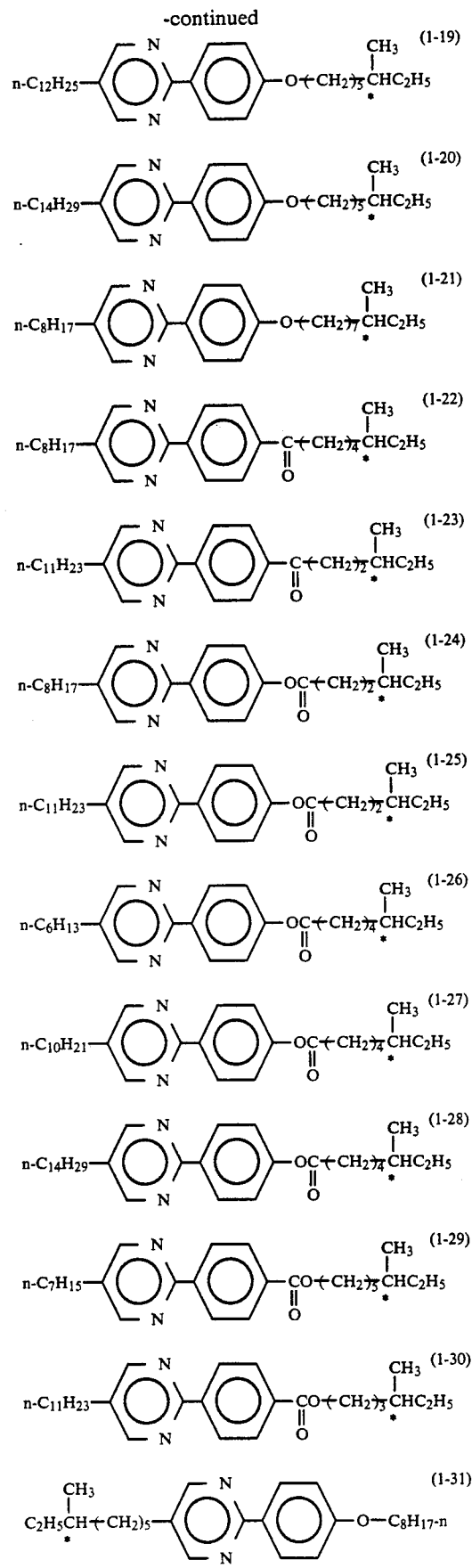

-continued

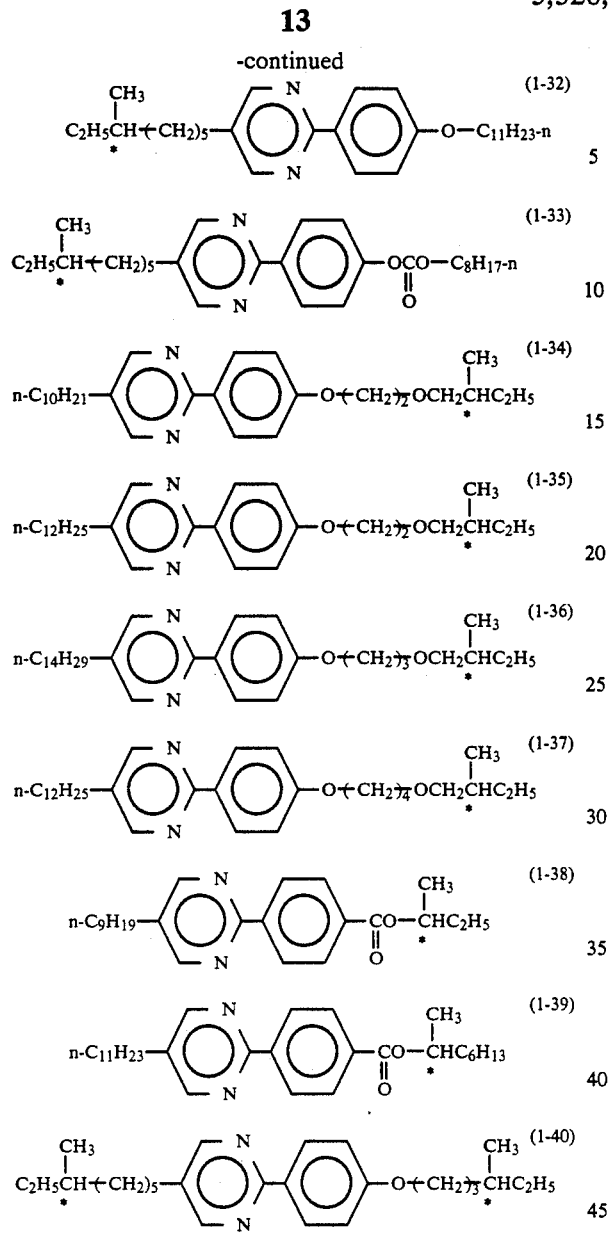

The compounds represented by the formula (I) may be synthesized through processes as disclosed by, e.g., Japanese Laid-Open Patent Applications (KOKAI) 93170/1986, 24576/1986, 129170/1986 and 215372/1986. For example, the following reaction scheme may be used for the synthesis.

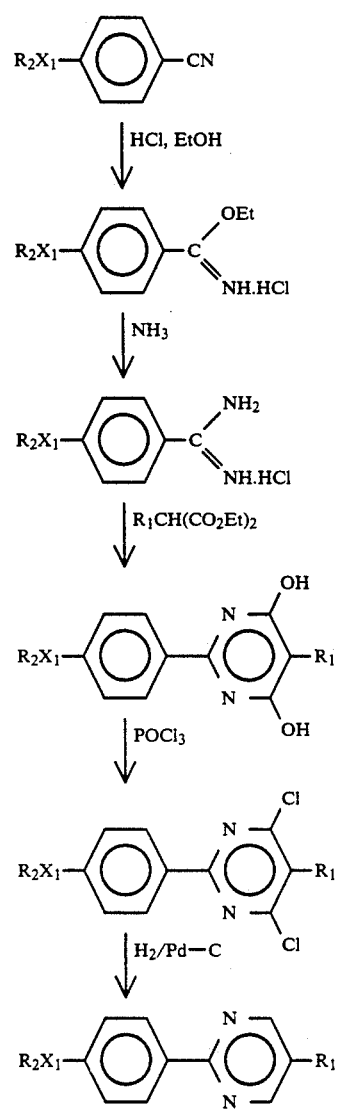

$R_1$, $R_2$ and $X_1$ are the same as defined above.

Specific examples of the compounds represented by the above-mentioned general formula (II) may include those shown by the following structural formulas.

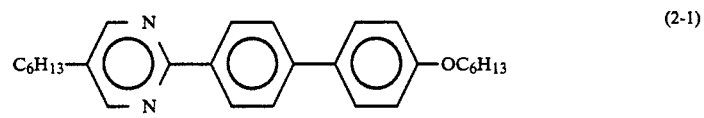

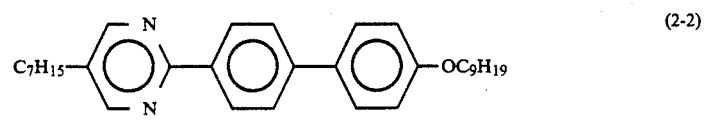

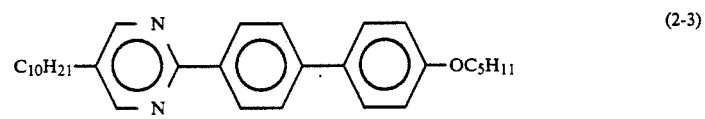

-continued
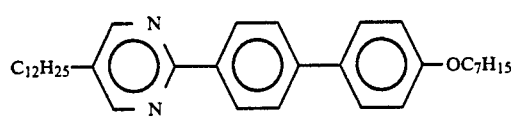  (2-4)
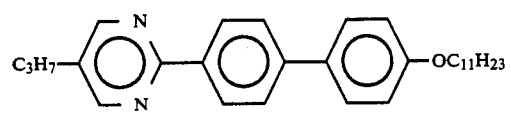  (2-5)
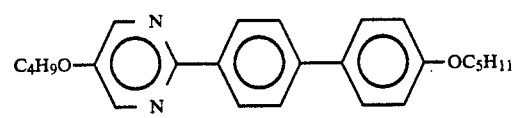  (2-6)
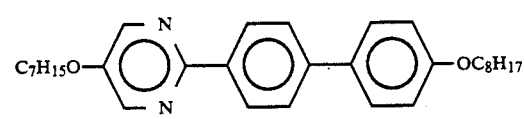  (2-7)
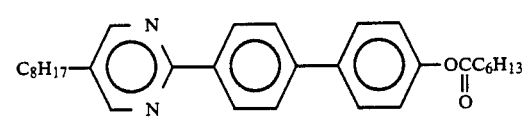  (2-8)
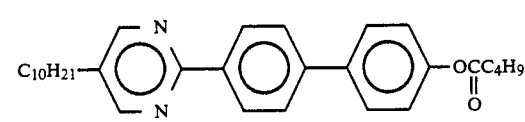  (2-9)
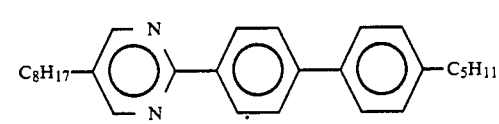  (2-10)
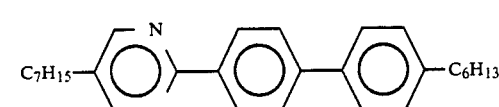  (2-11)
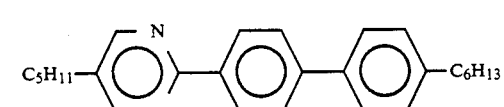  (2-12)
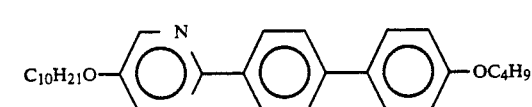  (2-13)
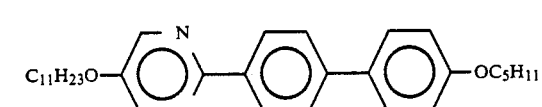  (2-14)
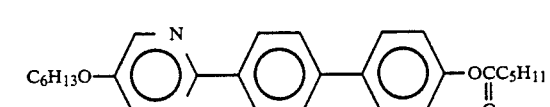  (2-15)
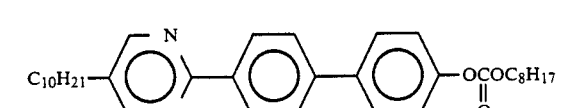  (2-16)

-continued
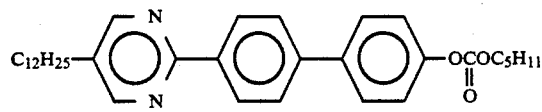 (2-17)
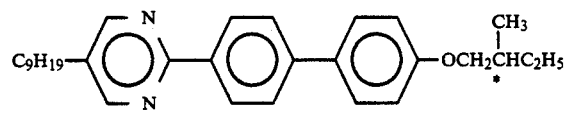 (2-18)
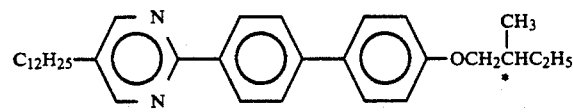 (2-19)
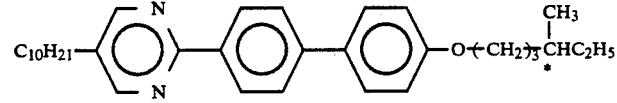 (2-20)
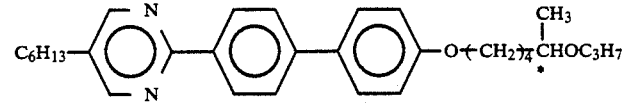 (2-21)
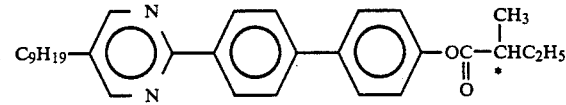 (2-22)
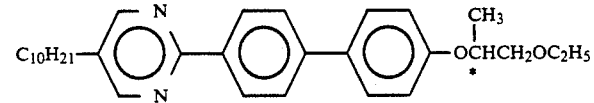 (2-23)
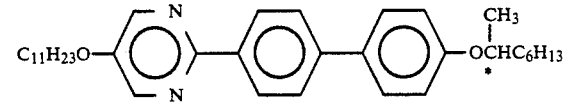 (2-24)
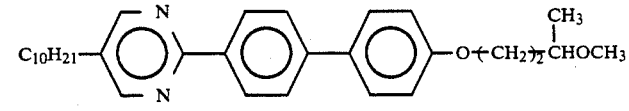 (2-25)
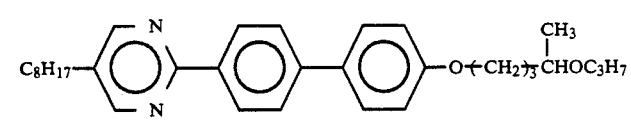 (2-26)
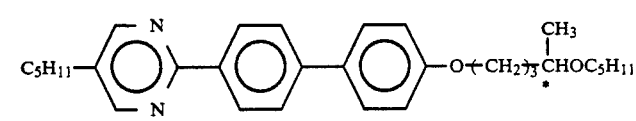 (2-27)
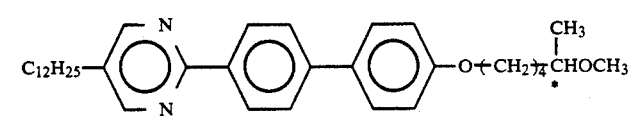 (2-28)
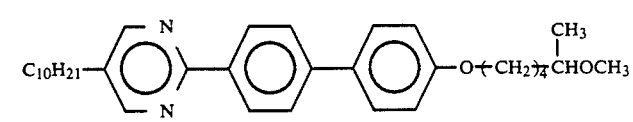 (2-29)

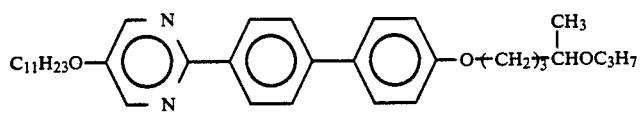 (2-30)
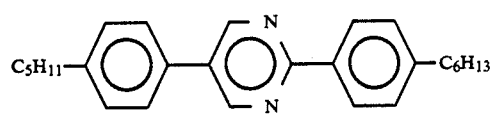 (2-31)
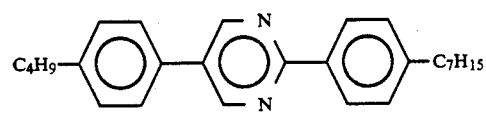 (2-32)
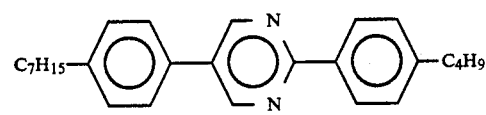 (2-33)
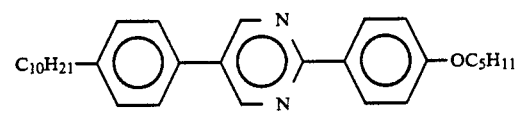 (2-34)
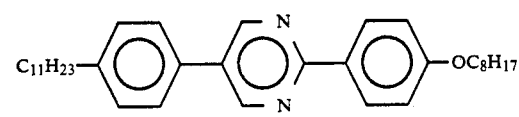 (2-35)
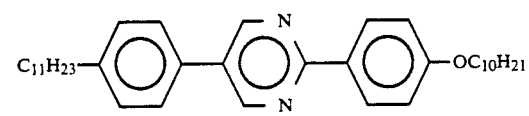 (2-36)
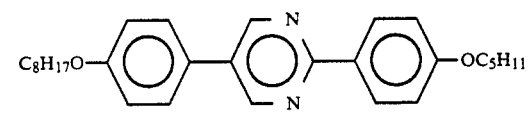 (2-37)
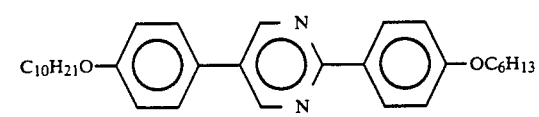 (2-38)
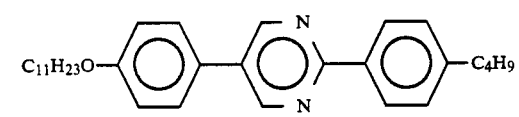 (2-39)
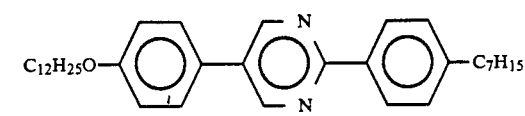 (2-40)
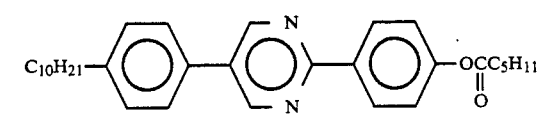 (2-41)
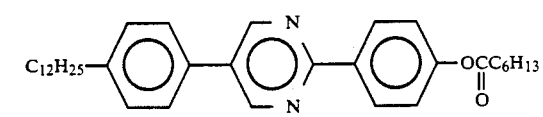 (2-42)

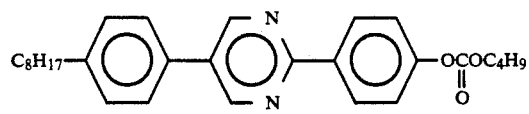 (2-43)
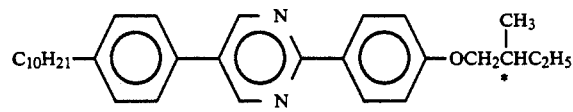 (2-44)
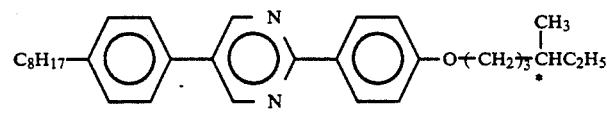 (2-45)
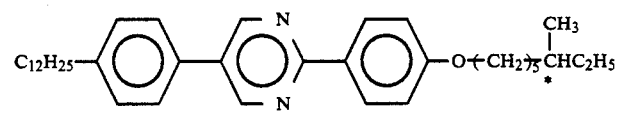 (2-46)
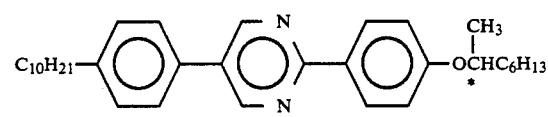 (2-47)
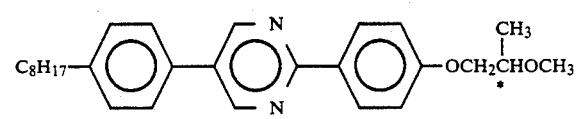 (2-48)
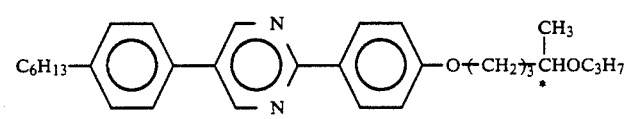 (2-49)
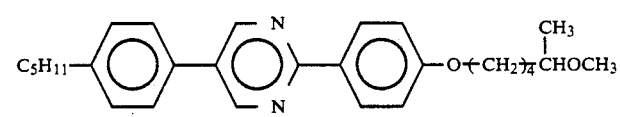 (2-50)
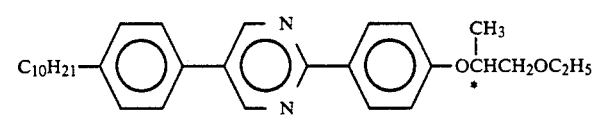 (2-51)
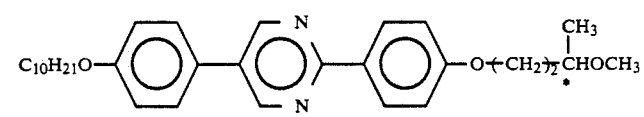 (2-52)
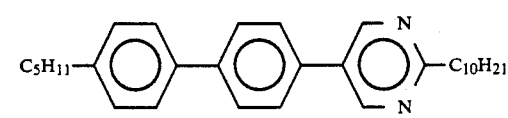 (2-53)
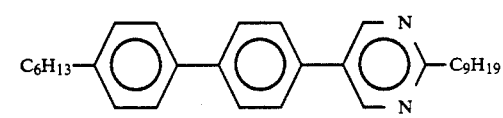 (2-54)
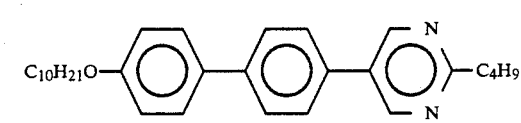 (2-55)

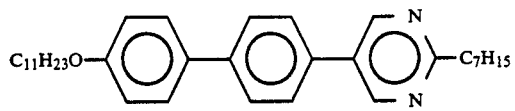
(2-56)
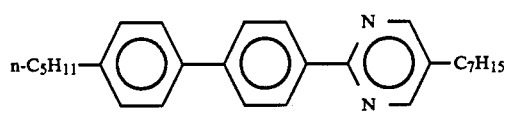
(2-57)
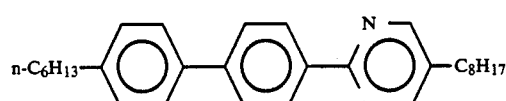
(2-58)
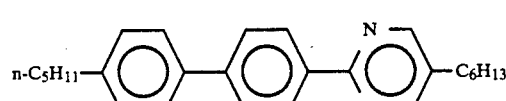
(2-59)
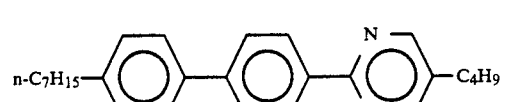
(2-60)
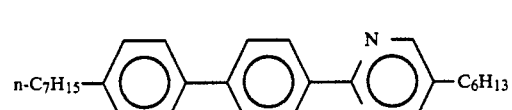
(2-61)
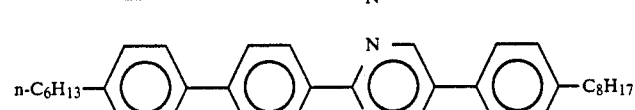
(2-62)
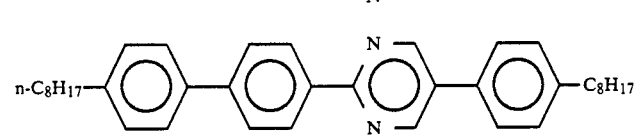
(2-63)
The compounds represented by the formula (II) may be synthesized through process as disclosed by, e.g., Japanese Patent Publication (KOKOKU) 5434/1987. More specifically, for example, compounds represented by the formula:
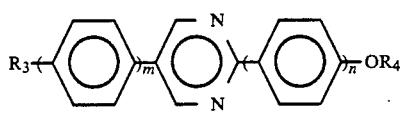
may be synthesized through the following reaction scheme:
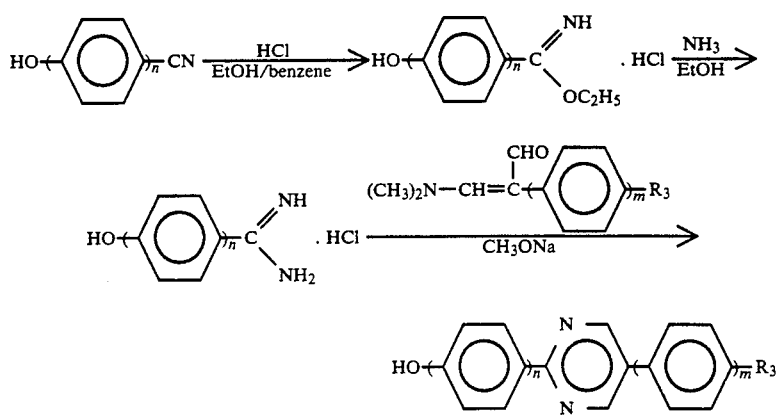

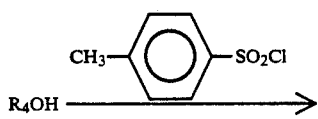
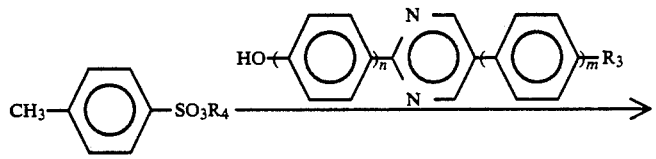
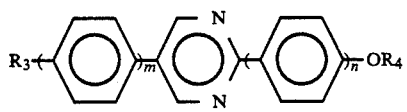

$R_3$, $R_4$, m and n are the same as defined above.

In a preferred embodiment, the ferroelectric chiral smectic liquid crystal composition according to the present invention further comprises a mesomorphic compound having a negative dielectric anisotropy, which is preferably selected from those represented by the following formulas (III-1) to (III-5):

Formula (III-1):

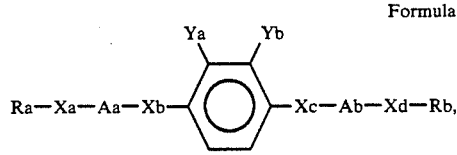

wherein Ra and Rb respectively denote a linear or branched alkyl group capable of having a substituent; Xa and Xd respectively denote a single bond, —O—,

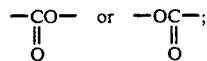

Xb and Xc respectively denote a single bond,

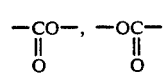

or —CH$_2$CH$_2$—; Aa and Ab respectively denote a single bond,

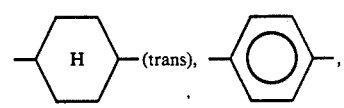

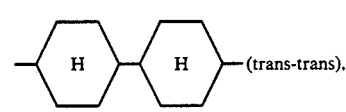

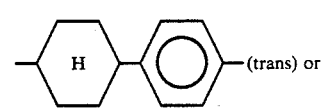

-continued

with proviso that when Aa and Ab are both single bonds, Xb and Xc are both single bonds, and Xa and Xd are both single bonds or —O—, or Xa is

and Xd is

and Ya and Yb are respectively cyano group, halogen or hydrogen with proviso that Ya and Yb cannot be hydrogen simultaneously;

Formula (III-2):

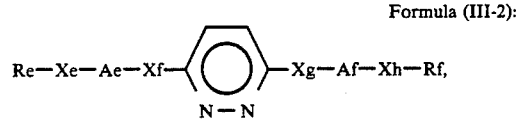

wherein Re and Rf respectively denote a linear or branched alkyl group capable of having a substituent; Xe and Xh are respectively a single bond, —O—,

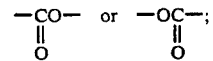

Xf and Xg are respectively

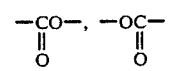

or a single bond; and Ae and Af are respectively

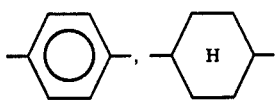

or a single bond with proviso that Ae and Af cannot be a single bond simultaneously;

Formula (III-3):

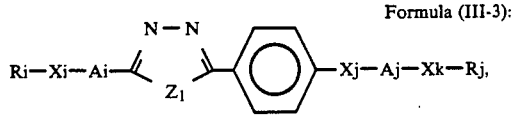

wherein Ai is a single bond or

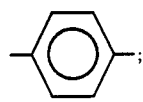

Aj is a single bond,

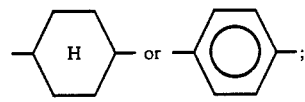

Ri and Rj are respectively a linear or branched alkyl group capable of having a substituent with proviso that Ri and Rj are linear alkyl groups when Aj is a single bond; $Z_1$ is —O— or —S—; Xi and Xk are respectively a single bond, —O—, —CO—, —OC— or —OCO—;
 ‖        ‖        ‖
 O        O        O Xj is a single bond,

—CO— —OC—,
 ‖       ‖
 O       O

—CH$_2$O— or —OCH$_2$ with proviso that Xi is a single bond when Ai is a single bond, Xj is not a single bond when Aj is

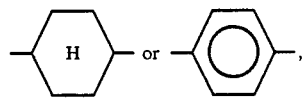

and Xk is a single bond when Aj is a single bond;

Formula (III-4):

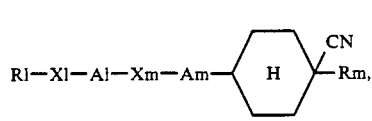

wherein Rl and Rm are respectively a linear or branched alkyl group capable of having a substituent; Al and Am are respectively a single bond,

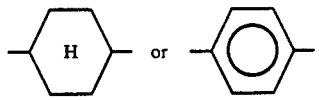

with proviso that Al and Am cannot be a single bond simultaneously; Xl is a single bond, —O—, —CO— or —OC—;
 ‖       ‖
 O       O and Xm is a single bond, —CO—, or —OC—,
 ‖        ‖
 O        O —CH$_2$O—, —OCH$_2$—, —CH$_2$CH$_2$— or —C≡C—;

Formula(III-5):

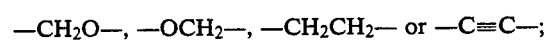

wherein Rn and Ro are respectively a linear or branched alkyl group capable of having a substituent; Xn and Xq are respectively a single bond, —O—, —CO— or —OC—;
 ‖       ‖
 O       O Xo and Xp are respectively a single bond, —CO—, or —OC—,
 ‖        ‖
 O        O —CH$_2$O—, —OCH$_2$— or —CH$_2$CH$_2$—; An and Ap are respectively a single bond,

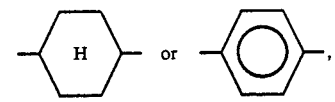

Ao is 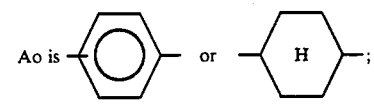;

and $Z_2$ is —C=CH— or —CH—CH$_2$—.
           |              |
           CN             CN In the above formulas (III-1) to (III-5), the alkyl groups Ra-Ro may respectively have 1-18 carbon atoms, preferably 4-16 carbon atoms, further preferably 6-12 carbon atoms.

Specific examples of mesomorphic compounds represented by the general formulas (III-1) to (III-5) may respectively include those denoted by the structural formulas shown below.

Formula (III-1)
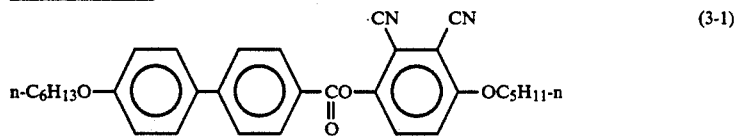 (3-1)
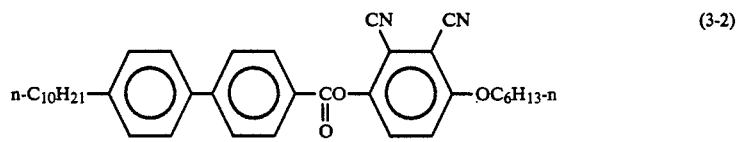 (3-2)
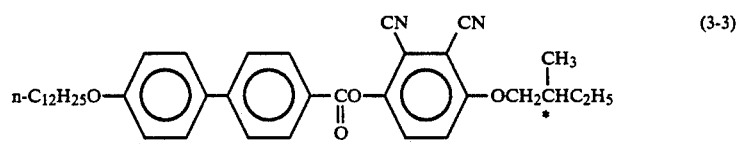 (3-3)
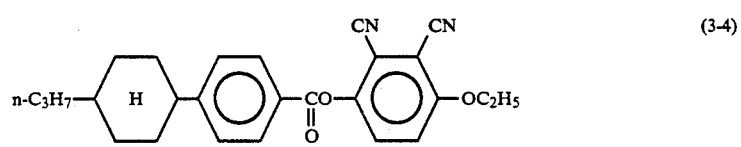 (3-4)
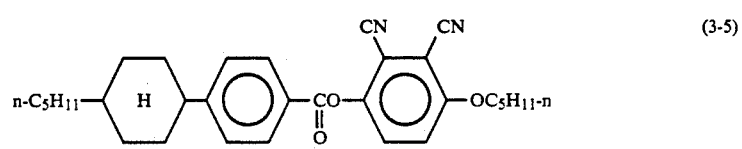 (3-5)
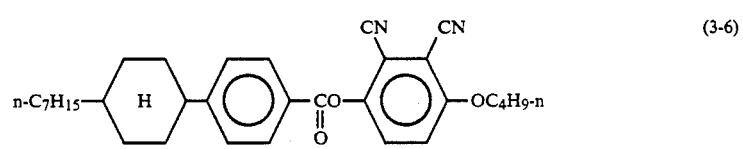 (3-6)
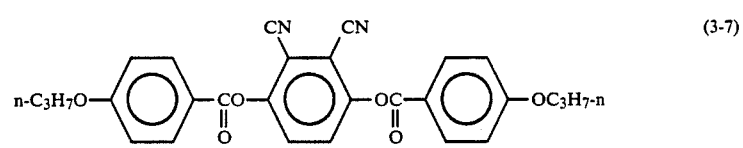 (3-7)
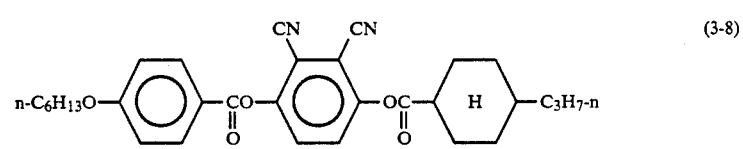 (3-8)
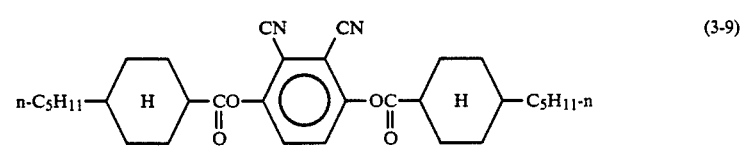 (3-9)
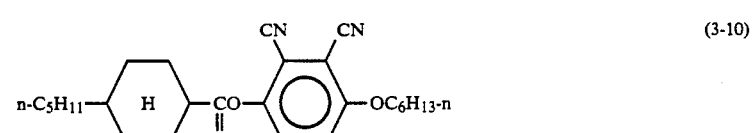 (3-10)
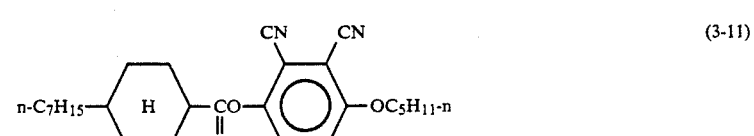 (3-11)

-continued
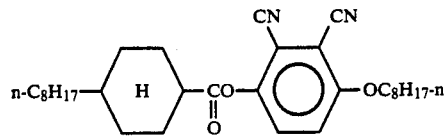 (3-12)
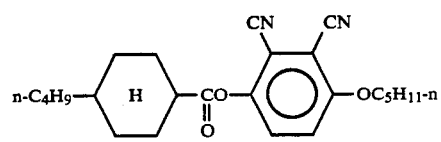 (3-13)
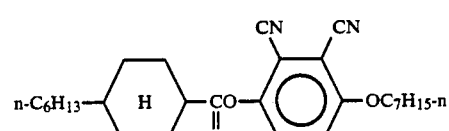 (3-14)
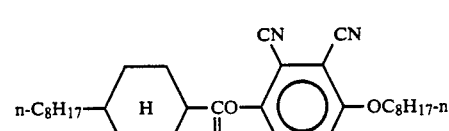 (3-15)
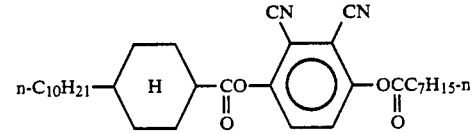 (3-16)
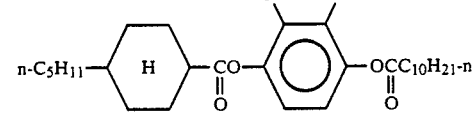 (3-17)
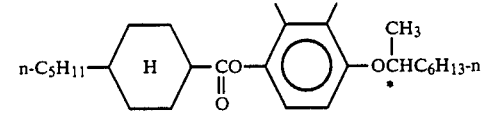 (3-18)
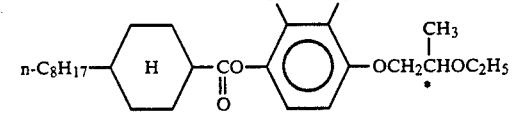 (3-19)
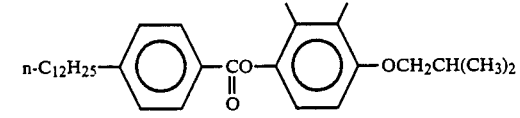 (3-20)
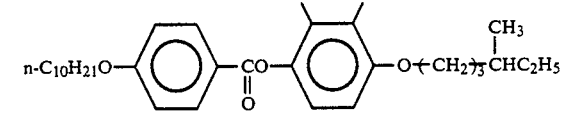 (3-21)
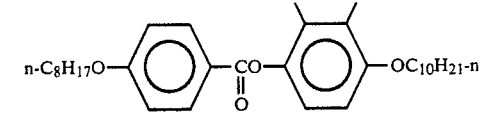 (3-22)

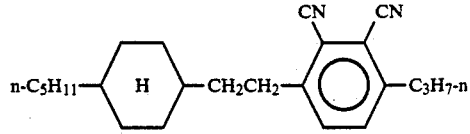 (3-23)
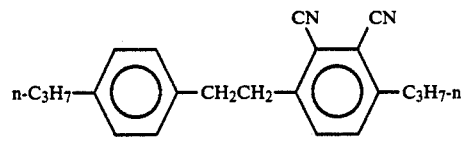 (3-24)
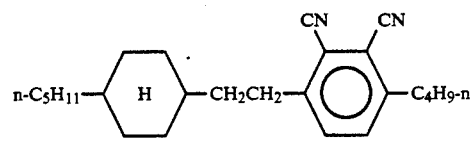 (3-25)
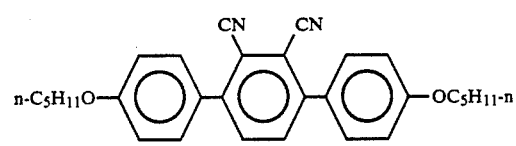 (3-26)
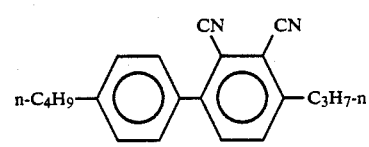 (3-27)
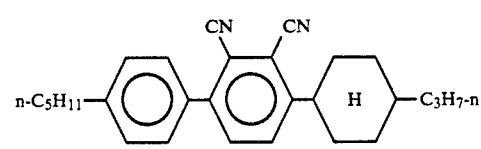 (3-28)
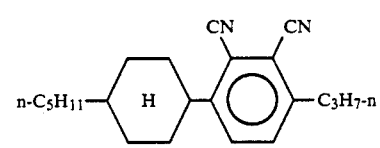 (3-29)
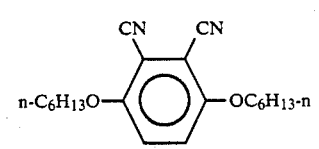 (3-30)
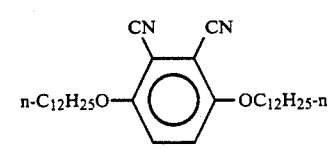 (3-31)
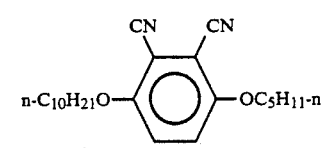 (3-32)
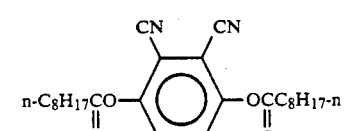 (3-33)

-continued
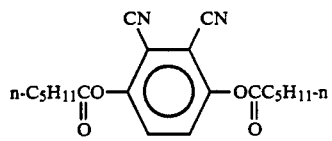 (3-34)
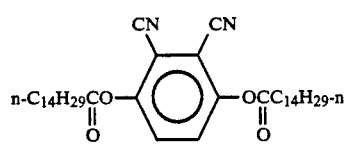 (3-35)
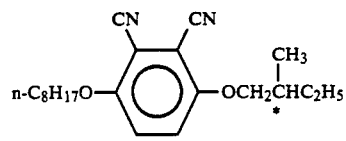 (3-36)
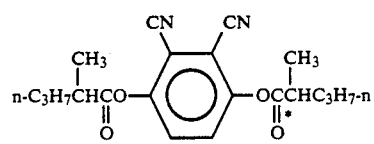 (3-37)
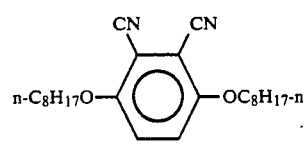 (3-38)
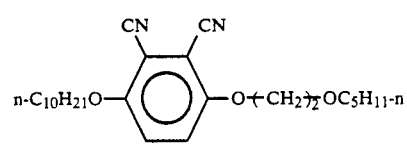 (3-39)
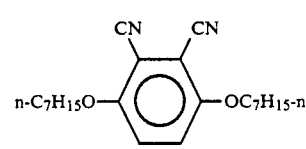 (3-40)
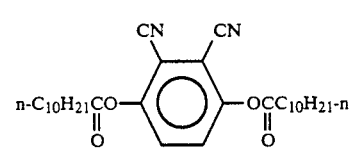 (3-41)
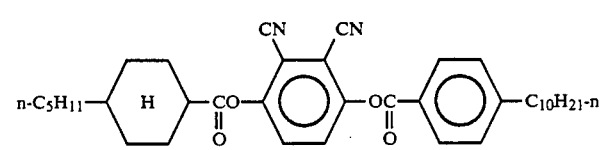 (3-42)
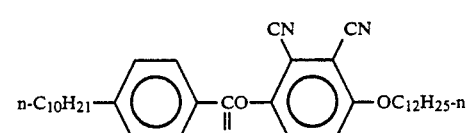 (3-43)
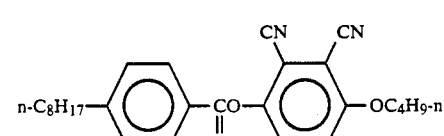 (3-44)

-continued
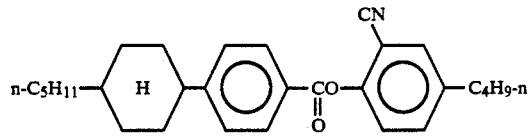 (3-45)
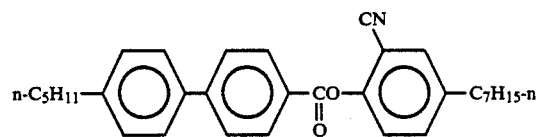 (3-46)
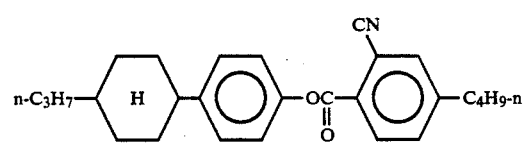 (3-47)
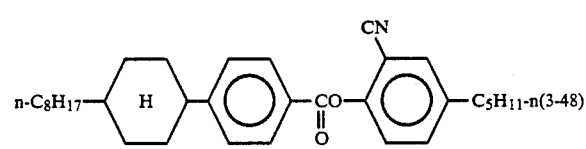 (3-48)
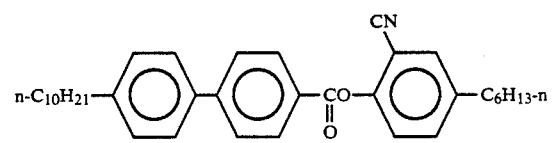 (3-49)
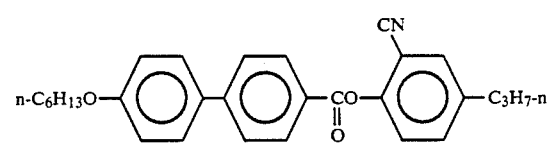 (3-50)
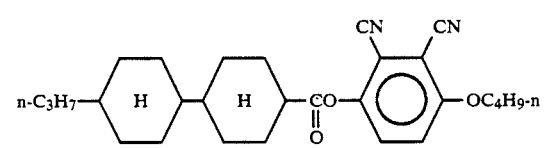 (3-51)
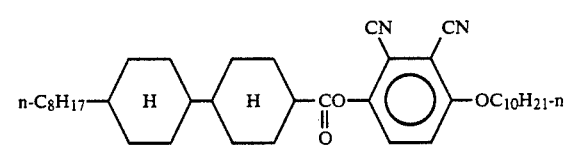 (3-52)
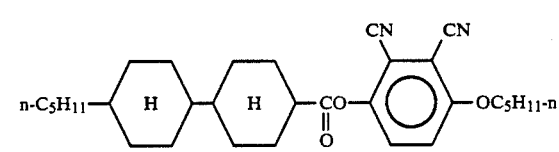 (3-53)
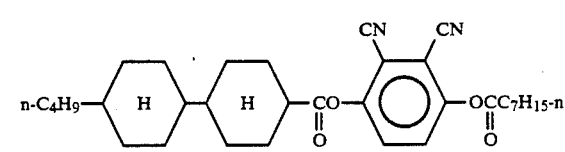 (3-54)
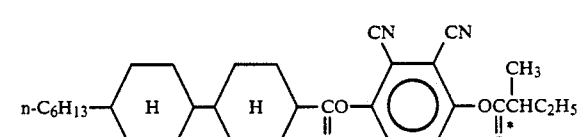 (3-55)

-continued
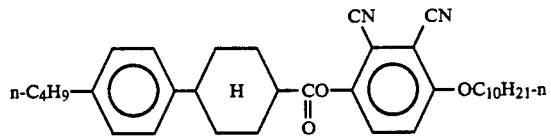 (3-56)
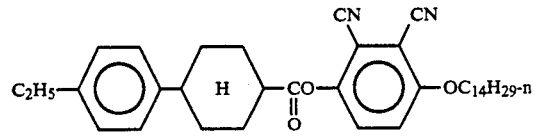 (3-57)
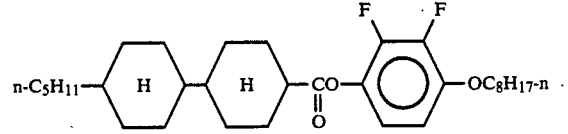 (3-58)
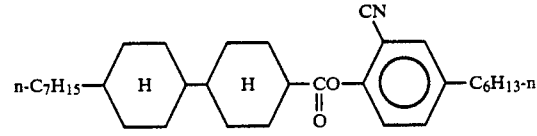 (3-59)
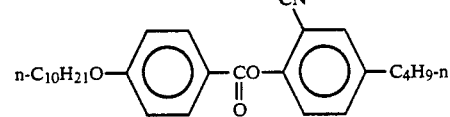 (3-60)
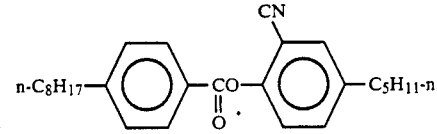 (3-61)
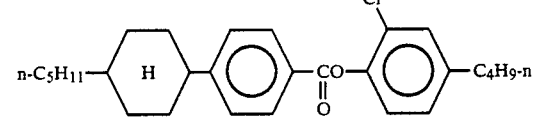 (3-62)
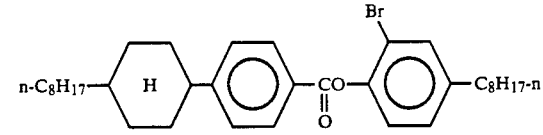 (3-63)
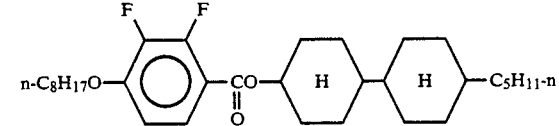 (3-64)
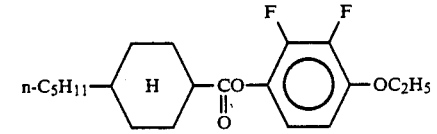 (3-65)
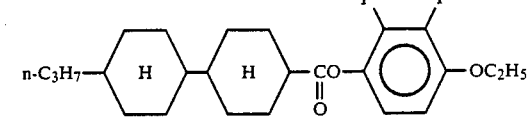 (3-66)

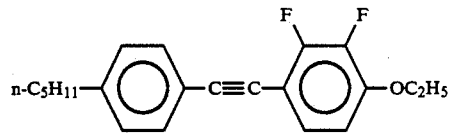
(3-67)
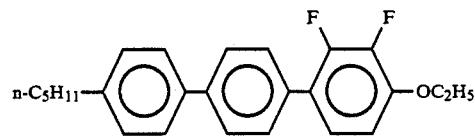
(3-68)
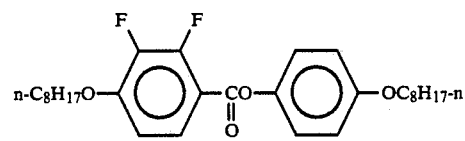
(3-69)
Formula (III-2)
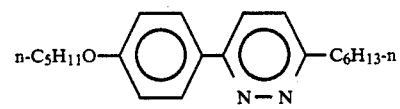
(3-70)
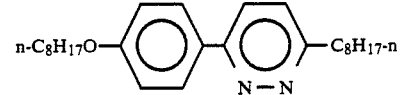
(3-71)
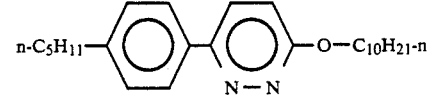
(3-72)
(3-73)
(3-74)
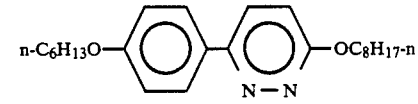
(3-75)
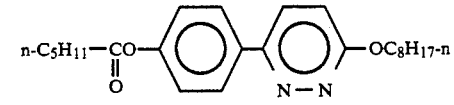
(3-76)
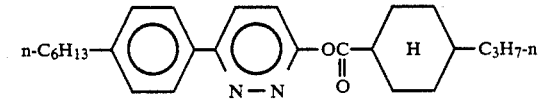
(3-77)
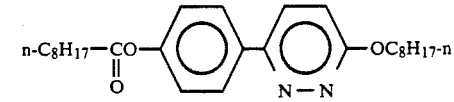
(3-78)

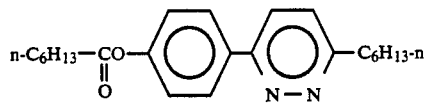 (3-79)
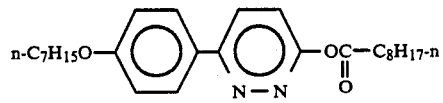 (3-80)
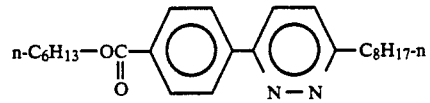 (3-81)
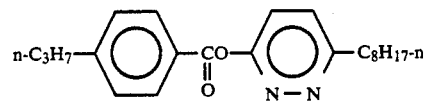 (3-82)
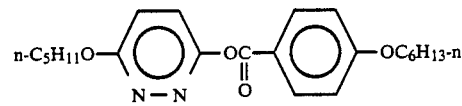 (3-83)
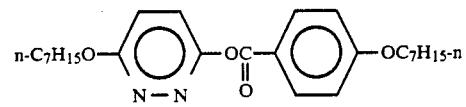 (3-84)
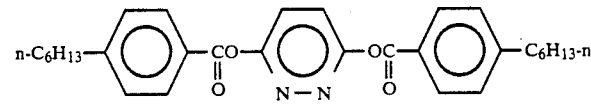 (3-85)
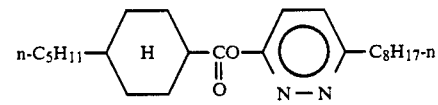 (3-86)
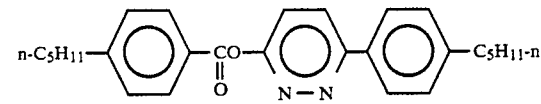 (3-87)
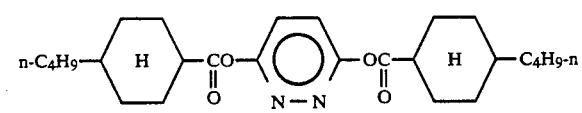 (3-88)
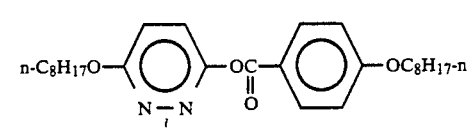 (3-89)
Formula (III-3)
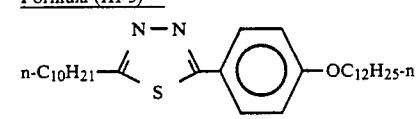 (3-90)
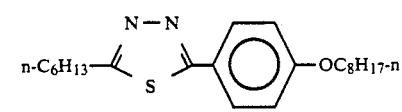 (3-91)

-continued
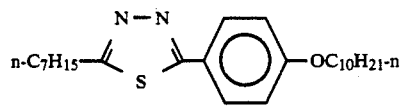 (3-92)
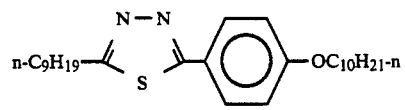 (3-93)
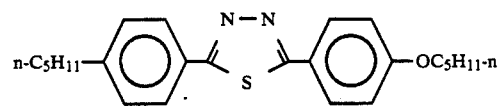 (3-94)
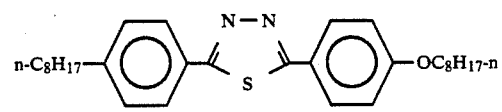 (3-95)
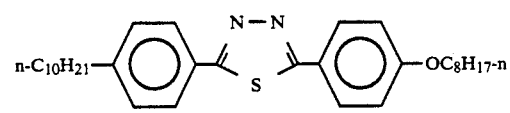 (3-96)
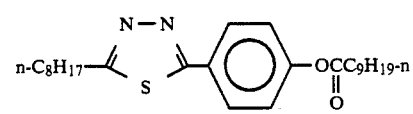 (3-97)
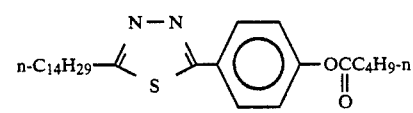 (3-98)
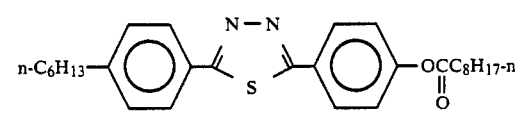 (3-99)
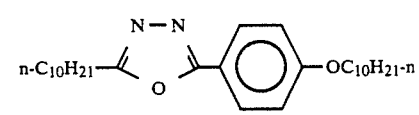 (3-100)
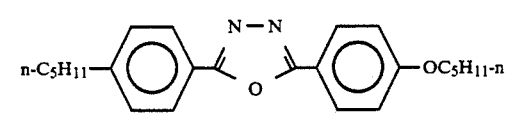 (3-101)
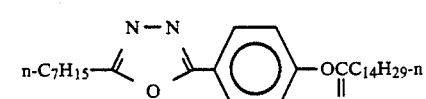 (3-102)
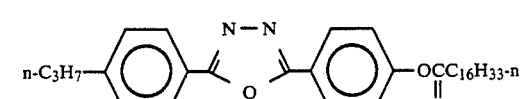 (3-103)
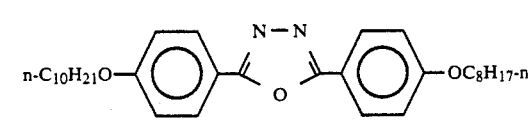 (3-104)

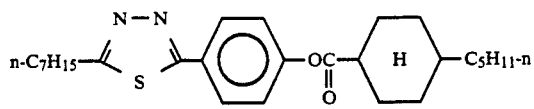 (3-105)
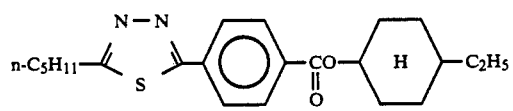 (3-106)
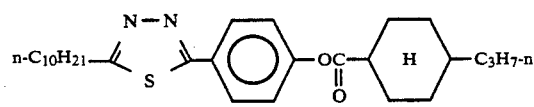 (3-107)
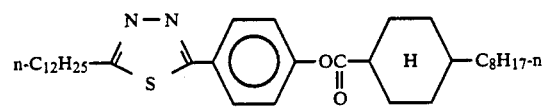 (3-108)
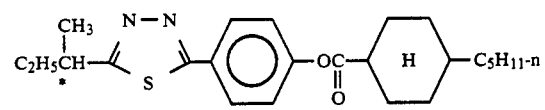 (3-109)
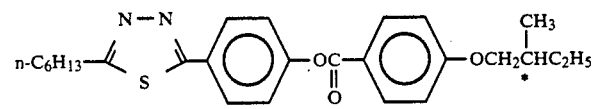 (3-110)
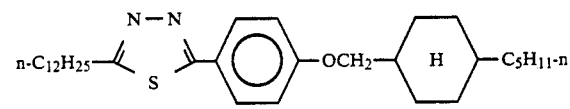 (3-111)
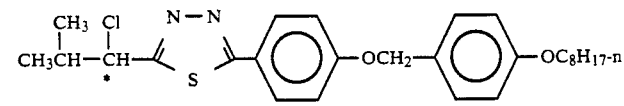 (3-112)
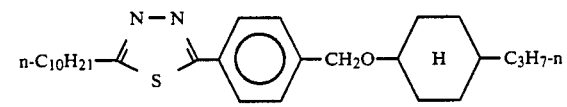 (3-113)
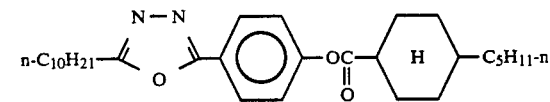 (3-114)
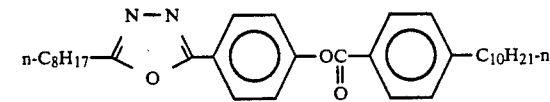 (3-115)
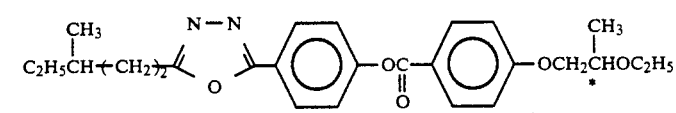 (3-116)
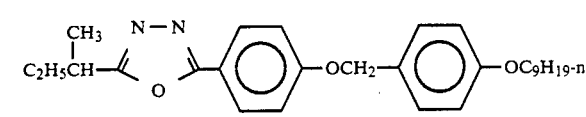 (3-117)

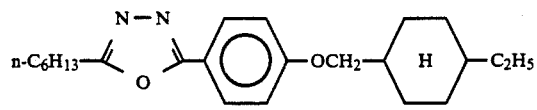 (3-118)
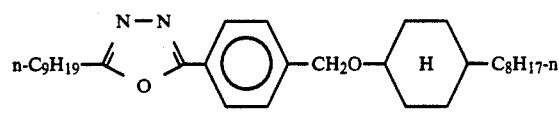 (3-119)
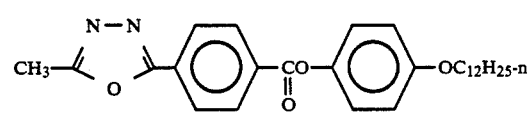 (3-120)
Formula (III-4)
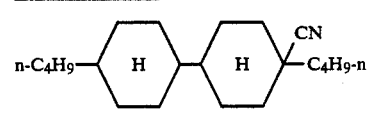 (3-121)
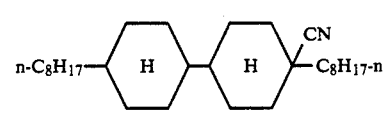 (3-122)
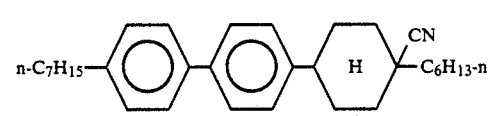 (3-123)
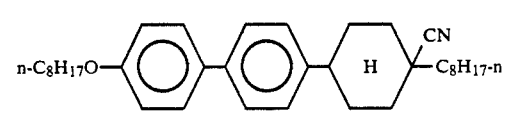 (3-124)
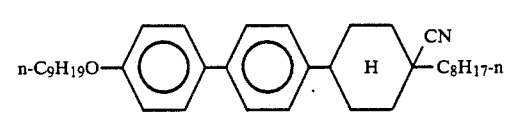 (3-125)
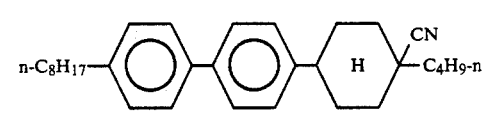 (3-126)
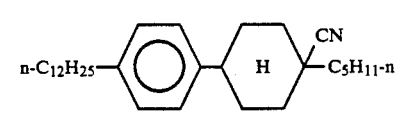 (3-127)
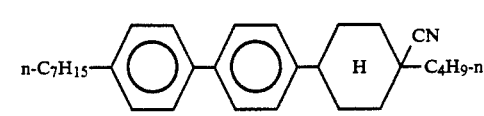 (3-128)
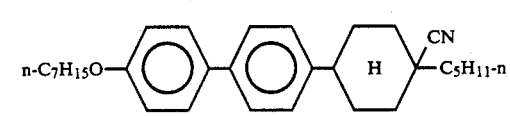 (3-129)
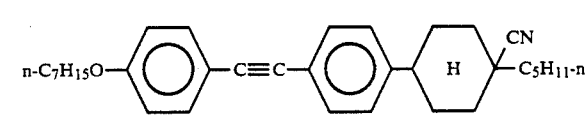 (3-130)

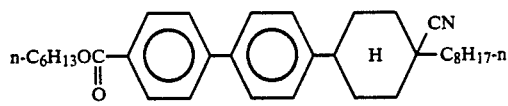 (3-131)
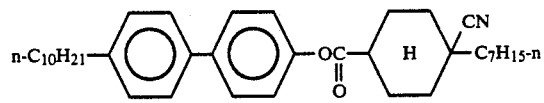 (3-132)
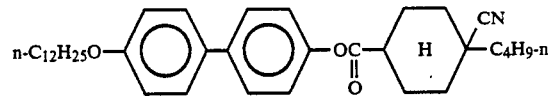 (3-133)
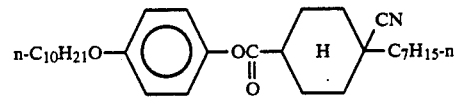 (3-134)
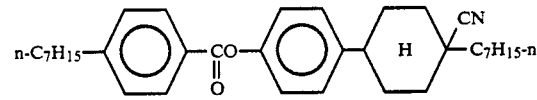 (3-135)
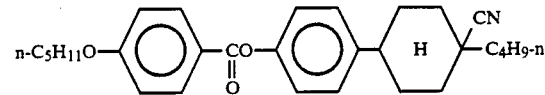 (3-136)
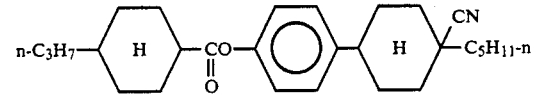 (3-137)
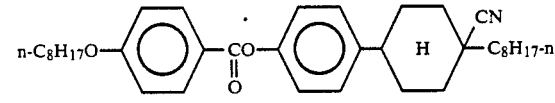 (3-138)
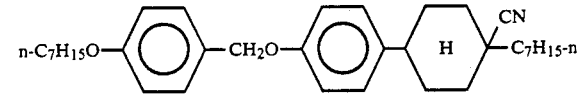 (3-139)
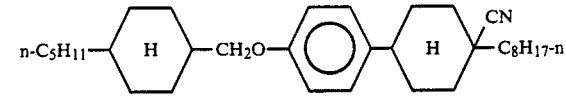 (3-140)
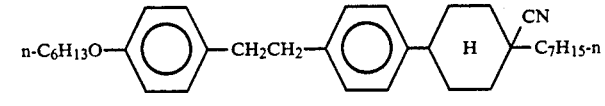 (3-141)
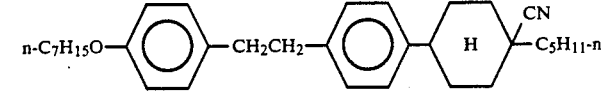 (3-142)
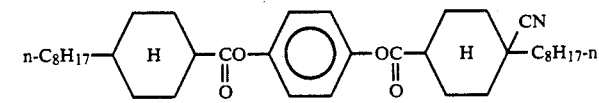 (3-143)
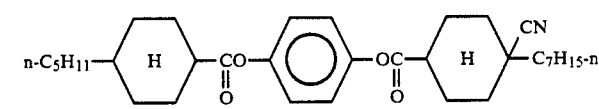 (3-144)

-continued
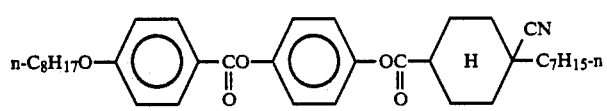 (3-145)
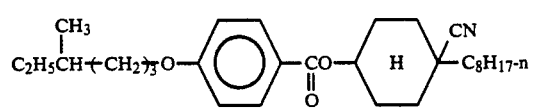 (3-146)
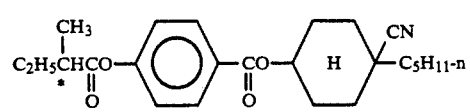 (3-147)
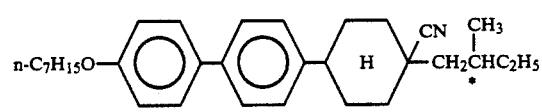 (3-148)
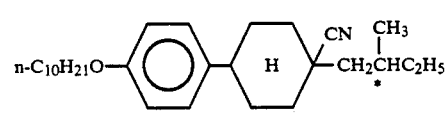 (3-149)
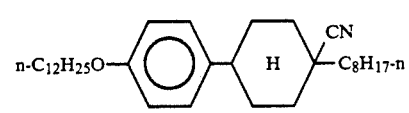 (3-150)
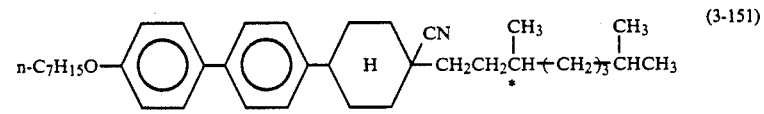 (3-151)
Formula (III-5)
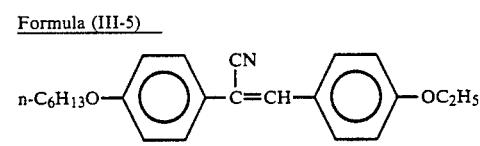 (3-152)
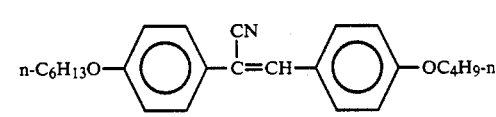 (3-153)
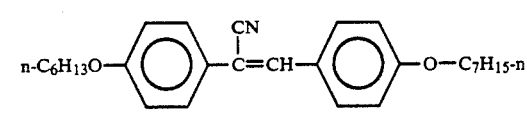 (3-154)
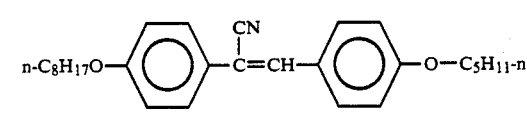 (3-155)
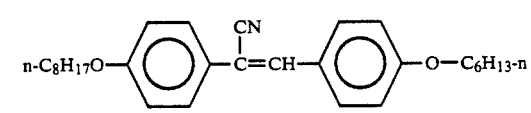 (3-156)
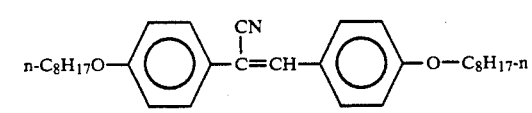 (3-157)

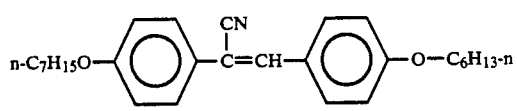
(3-158)
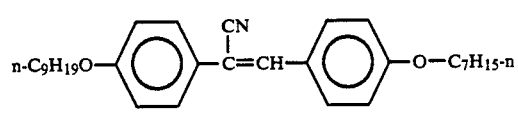
(3-159)
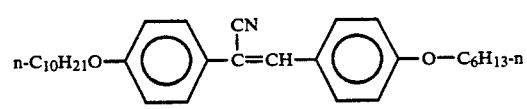
(3-160)
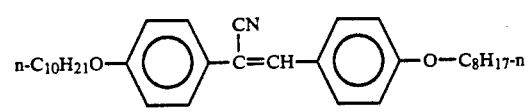
(3-161)
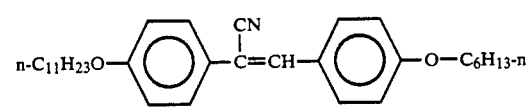
(3-162)
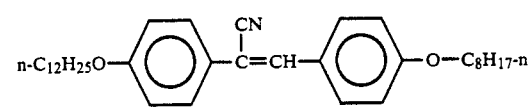
(3-163)
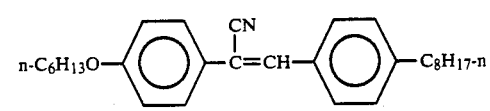
(3-164)
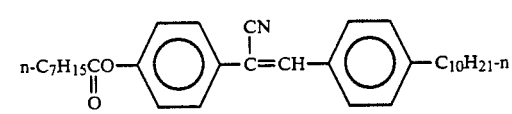
(3-165)
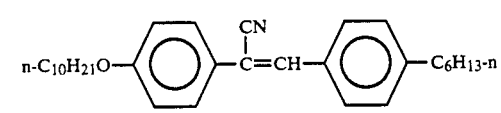
(3-166)
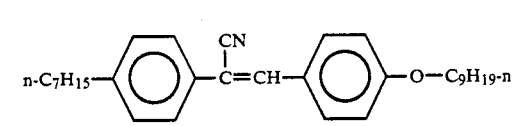
(3-167)
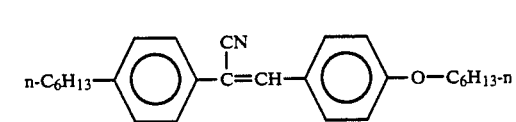
(3-168)
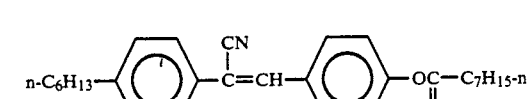
(3-169)
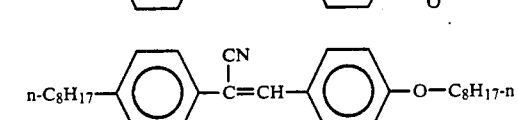
(3-170)
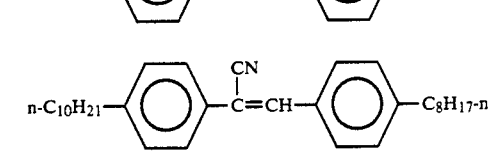
(3-171)

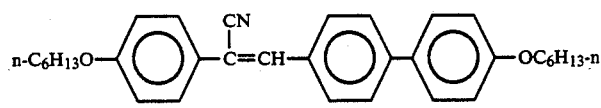 (3-172)
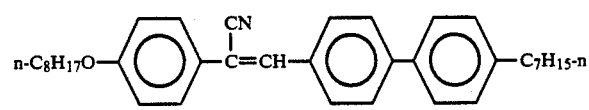 (3-173)
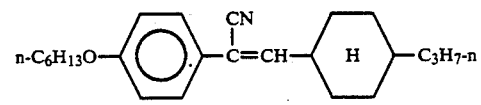 (3-174)
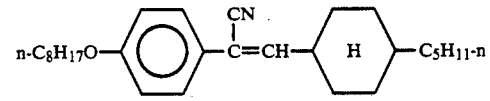 (3-175)
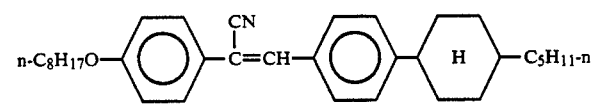 (3-176)
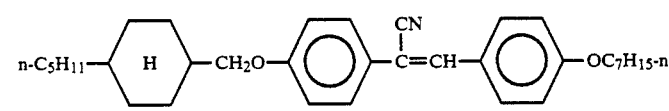 (3-177)
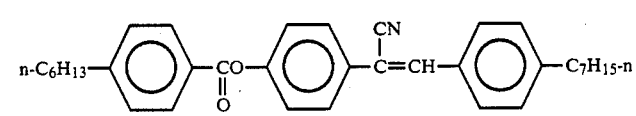 (3-178)
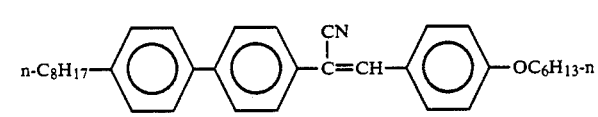 (3-179)
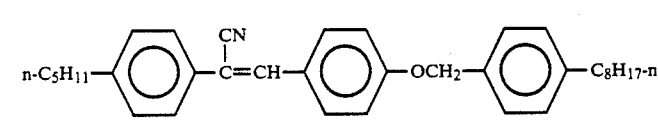 (3-180)
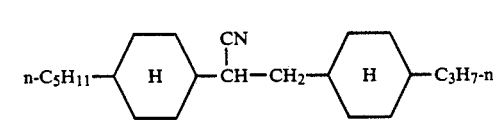 (3-181)
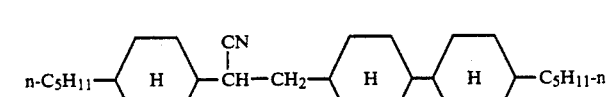 (3-182)
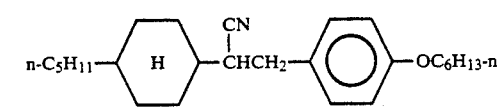 (3-183)
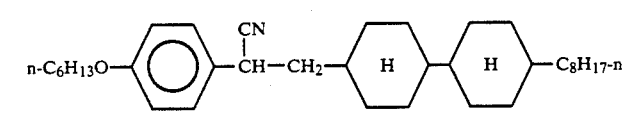 (3-184)

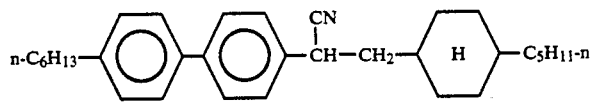
(3-185)

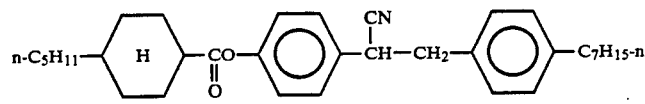
(3-186)

The mesomorphic compound having a negative dielectric anisotropy $\Delta\epsilon$ may preferably have $\Delta\epsilon < -2$, preferably $\Delta\epsilon < -5$, further preferably $\Delta\epsilon < -10$.

The liquid crystal composition according to the present invention may be obtained by mixing at least one species of the compound represented by the formula (I), at least one species of the compound represented by the formula (II), optionally at least one species of a mesomorphic compound having a negative dielectric anisotropy and another mesomorphic compound in appropriate proportions. The liquid crystal composition according to the present invention may preferably be formulated as a ferroelectric liquid crystal composition, particularly a ferroelectric chiral smectic liquid crystal composition.

Specific examples of another mesomorphic compound as described above may includes those denoted by the following structure formulas.

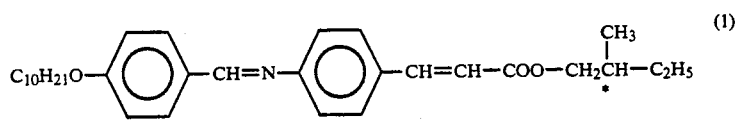
(1)

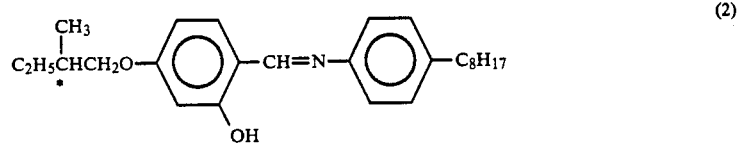
(2)

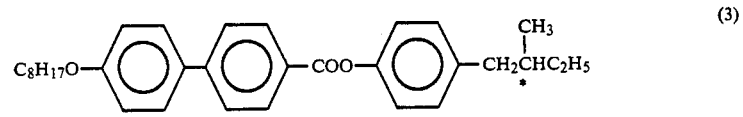
(3)

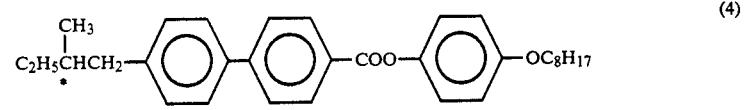
(4)

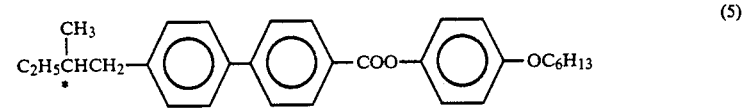
(5)

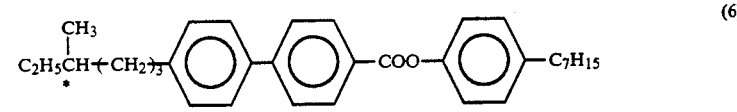
(6)

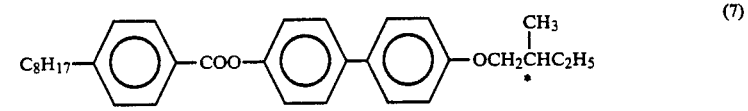
(7)

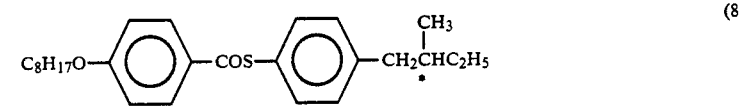
(8)

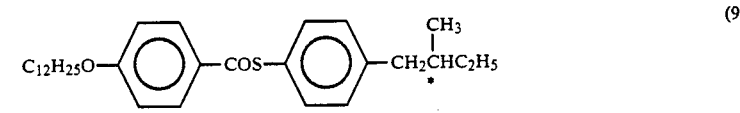
(9)

-continued
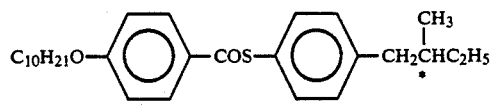 (10)
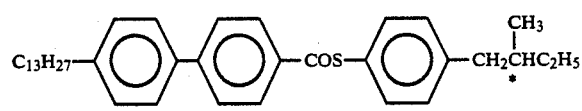 (11)
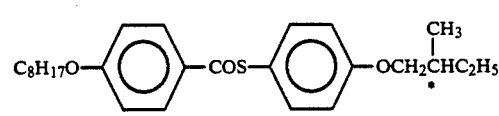 (12)
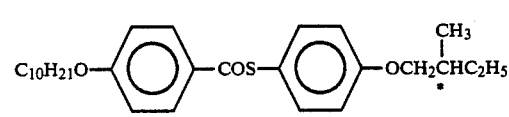 (13)
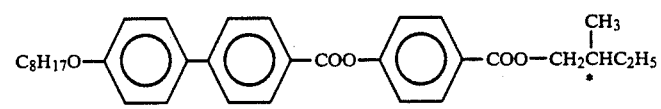 (14)
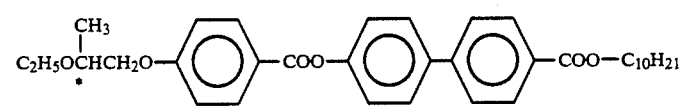 (15)
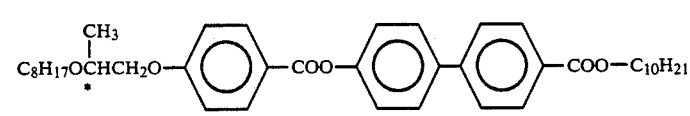 (16)
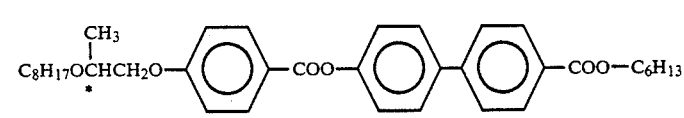 (17)
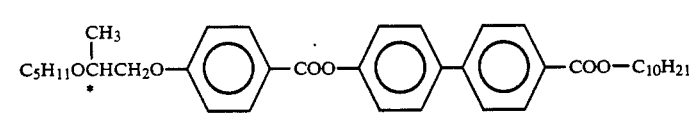 (18)
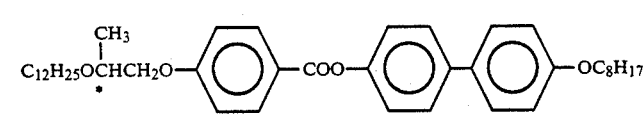 (19)
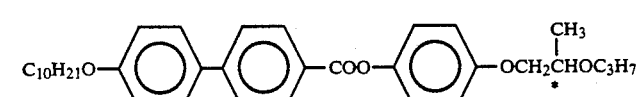 (20)
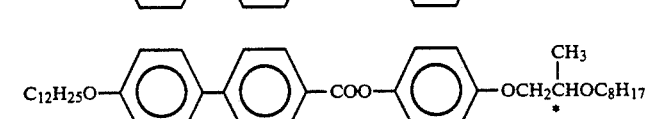 (21)
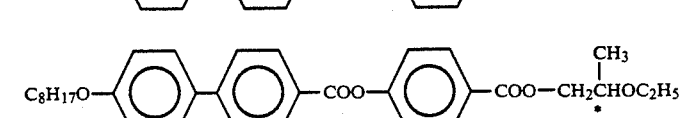 (22)
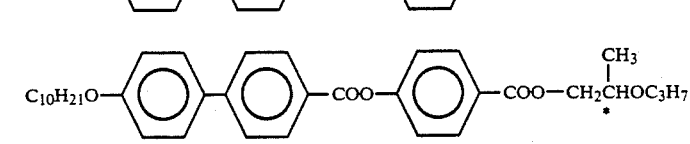 (23)

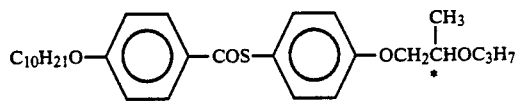
(24)
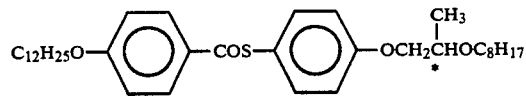
(25)
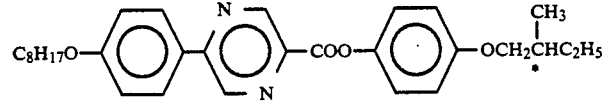
(26)
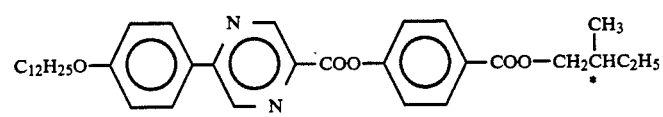
(27)
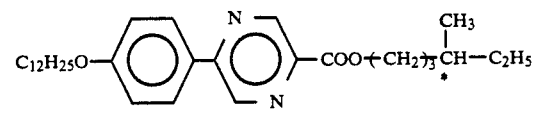
(28)
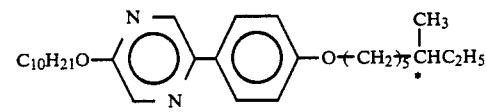
(29)
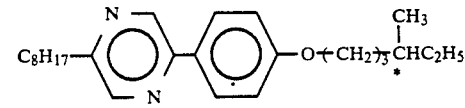
(30)
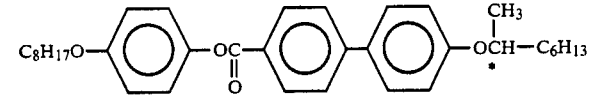
(31)
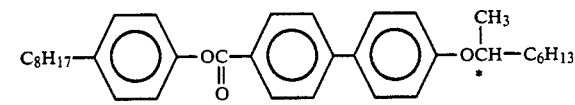
(32)
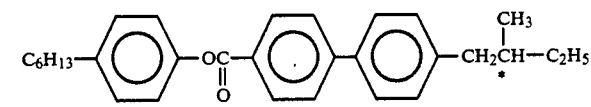
(33)
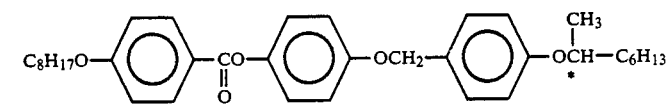
(34)
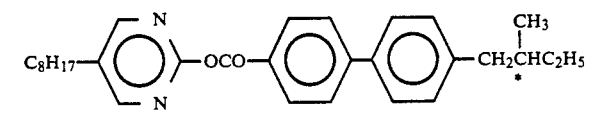
(35)
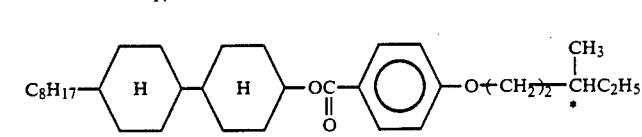
(36)

-continued
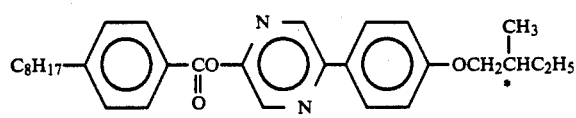 (37)
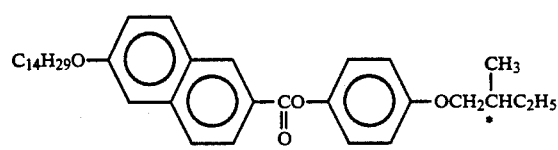 (38)
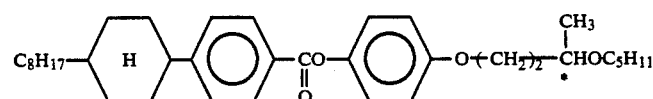 (39)
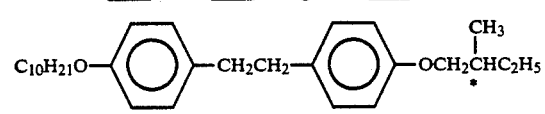 (40)
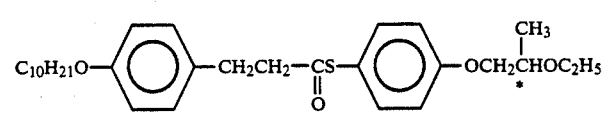 (41)
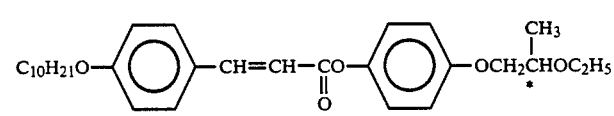 (42)
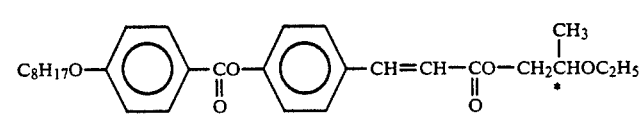 (43)
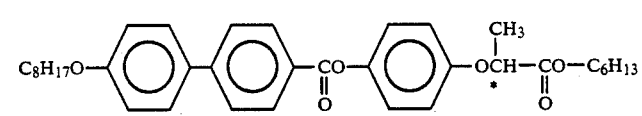 (44)
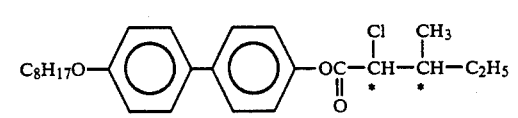 (45)
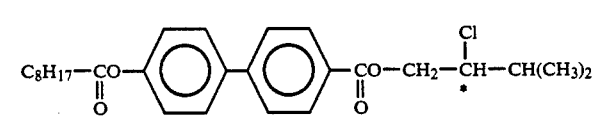 (46)
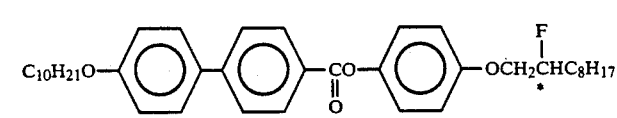 (47)
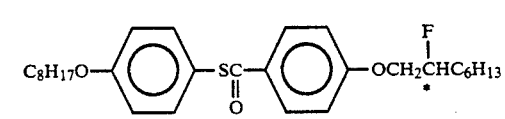 (48)
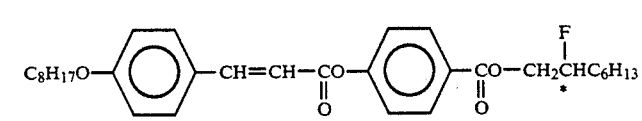 (49)

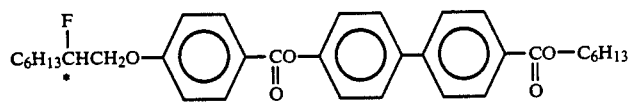 (50)
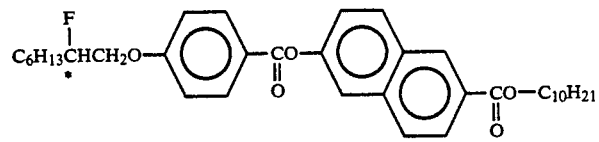 (51)
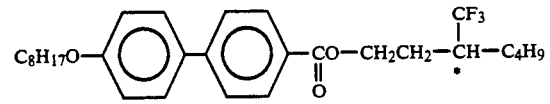 (52)
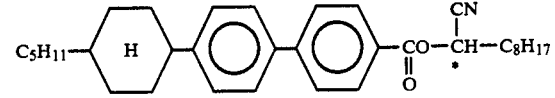 (53)
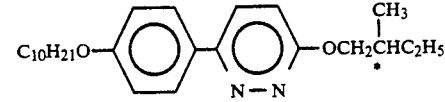 (54)
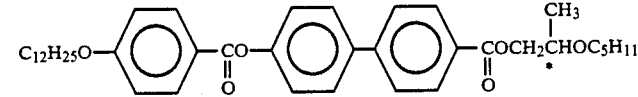 (55)
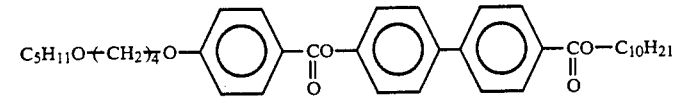 (56)
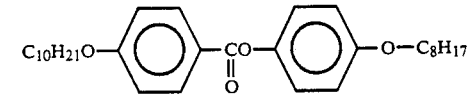 (57)
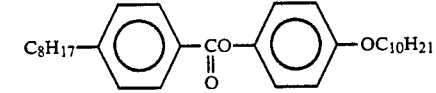 (58)
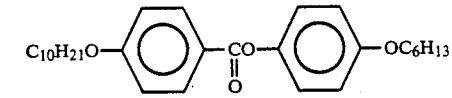 (59)
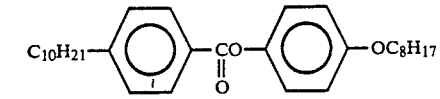 (60)
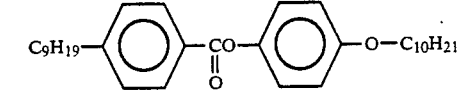 (61)
 (62)

-continued
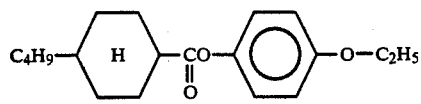
(63)
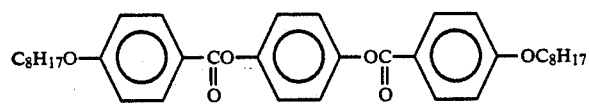
(64)
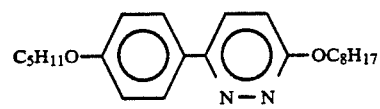
(65)
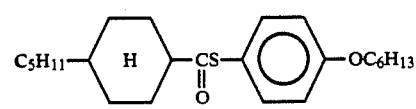
(66)
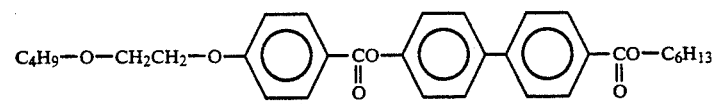
(67)
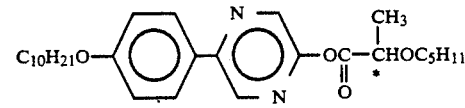
(68)
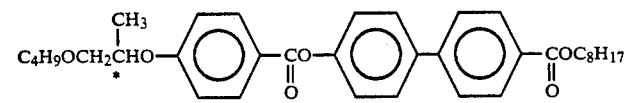
(69)
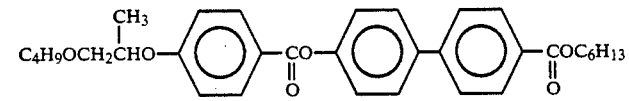
(70)
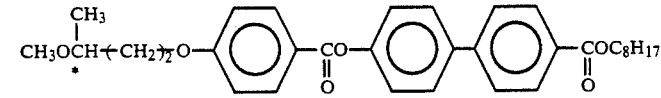
(71)
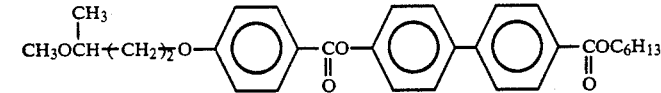
(72)
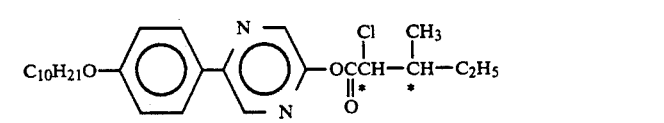
(73)
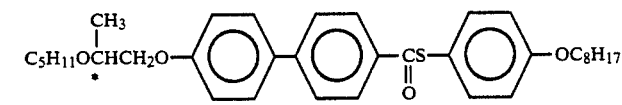
(74)
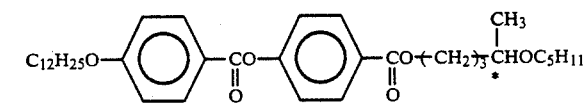
(75)
In formulating the liquid crystal composition according to the present invention, it is desirable to mix 1–300 wt. parts each, preferably 2–100 wt. parts each, of a compound represented by the formula (I) and a compound represented by the formula (II) with 100 wt.

parts of another mesomorphic compound as mentioned above which can be composed of two or more species.

Further, when two or more species of either one or both of the compounds represented by the formulas (I) and (II) are used, the two or more species of the compound of the formula (I) or (II) may be used in a total amount of 1-500 wt. parts, preferably 2-100 wt. parts, per 100 wt. parts of another mesomorphic compound as described above which can be composed of two or more species.

Further, the weight ratio of the compound of the formula (I)/the compound of the formula (II) may desirably be 1/300-300/1, preferably 1/50-50/1. When two or more species each of the compounds of the formulas (I) and (II) are used, the weight ratio of the total amount of the compounds of the formula (I)/the total amounts of the compounds of the formula (II) may desirably be 1/500-500/1, preferably 1/50-50/1.

Further, the total amounts of the compounds of the formulas (I) and (II) may desirably be 2-600 wt. parts, preferably 4-200 wt. parts, when one species each is selected from the formulas (I) and (II), or 2-1000 wt. parts, preferably 4-200 wt. parts, when two or more species are selected from at least one of the formulas (I) and (II), respectively, with respect to 100 wt. parts of the above-mentioned another mesomorphic compound which may be composed of two or more species.

Further, a mesomorphic compound having a negative dielectric anisotropy as described above can be contained in a proportion of 1-98 wt. % of the liquid crystal composition of the present invention so as to provide a composition having a negative dielectric anisotropy. Particularly, when a mesomorphic compound having $\Delta\epsilon < -2$ is used, it may be contained in a proportion of 1-70 wt. %, preferably 1-50 wt. %, of the liquid crystal composition of the present invention.

Further, the total of the compounds of the formulas (I) and (II) and the mesomorphic compound having a negative dielectric anisotropy can constitute 3-100 wt. % of the liquid crystal composition of the present invention.

The ferroelectric liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the ferroelectric liquid crystal device prepared as described above for explanation of the structure thereof.

Referring to FIG. 1, the ferroelectric liquid crystal device includes a ferroelectric liquid crystal layer 1 disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a selection of an organic insulating material or a precursor thereof in a concentration of 0.1 to 20 wt. %, preferably 0.2-10 wt. %, by spinner coating, dip coating, screen printing, spray coating or roller coating, followed by curing or hardening under prescribed hardening condition (e.g., by heating). The insulating alignment control layer may have a thickness of ordinarily 30 Å-1 micron, preferably 30-3000 Å, further preferably 50-1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a ferroelectric liquid crystal is sealed up to provide a ferroelectric liquid crystal layer 1 in a thickness of generally 0.5 to 20 microns, preferably 1 to 5 microns.

The ferroelectric liquid crystal provided by the composition of the present invention may desirably assume a SmC* phase (chiral smectic C phase) in a wide temperature range including room temperature (particularly, broad in a lower temperature side) and also shows wide drive voltage margin and drive temperature margin when contained in a device.

Particularly, in order to show a good alignment characteristic to form a uniform monodomain, the ferroelectric liquid crystal may show a phase transition series comprising isotropic phase—Ch phase (cholesteric phase)—SmA phase (smectic A phase)—SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
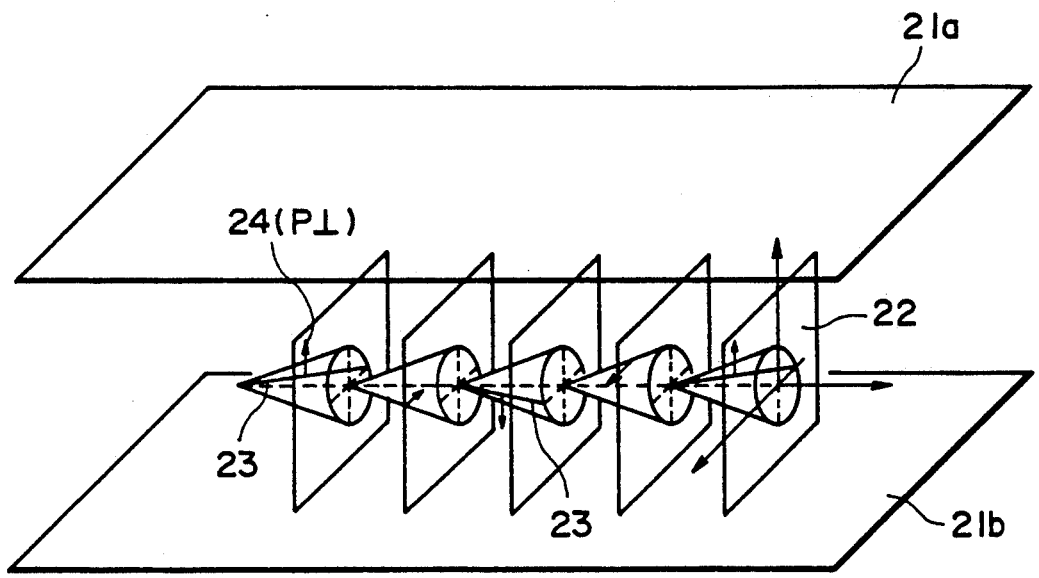
FIGS. 2 and 3 are schematic perspective views of a device cell embodiment for illustrating the operation principle of a ferroelectric liquid crystal device.

FIG. 2 is a schematic illustration of a ferroelectric liquid crystal cell (device) for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
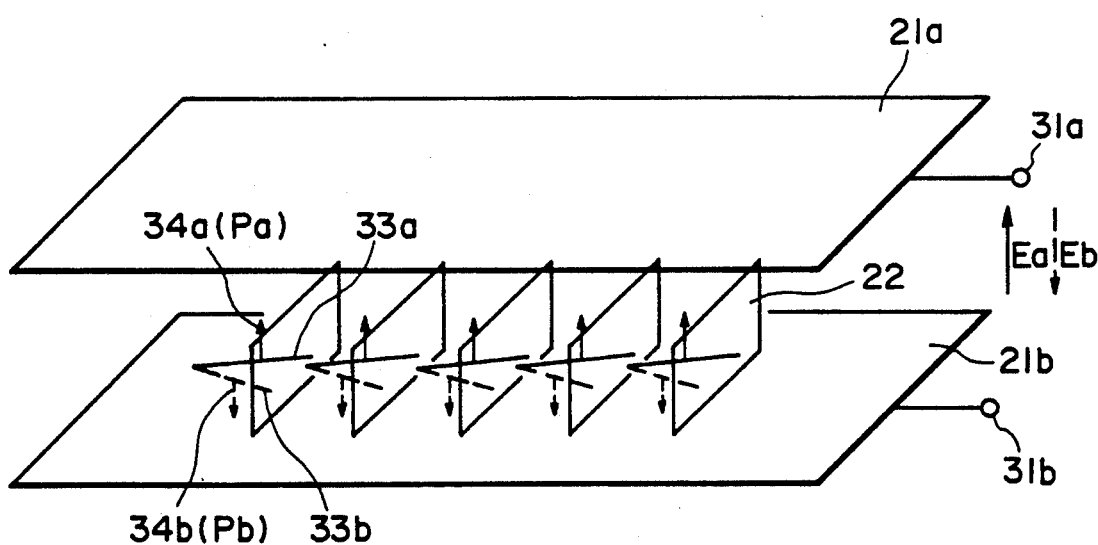

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

When such a ferroelectric liquid crystal device comprising a ferroelectric liquid crystal composition as described above between a pair of electrode plates is constituted as a simple matrix display device, the device may be driven by a driving method as disclosed in Japanese Laid-Open Patent Applications (KOKAI) Nos. 193426/1984, 193427/1984, 046/1985, 156047/1985, etc.

More specifically, such a ferroelectric liquid crystal device may for example be driven by a driving embodiment as described hereinbefore with reference to FIGS. 3 to 7.

Hereinbelow, the present invention will be explained more specifically with reference to examples. It is however to be understood that the present invention is not restricted to these examples.

EXAMPLE 1

A liquid crystal composition 1-A was prepared by mixing the following compounds in respectively indicated proportions.

| Ex. Compound No. | Structural formula | Wt. parts |
|---|---|---|
| 8 | $C_8H_{17}O$—⟨O⟩—COS—⟨O⟩—$CH_2\overset{*}{C}HC_2H_5$ with $CH_3$ branch | 40 |
| 9 | $C_{12}H_{25}O$—⟨O⟩—COS—⟨O⟩—$CH_2\overset{*}{C}HC_2H_5$ with $CH_3$ branch | 40 |
| 12 | $C_8H_{17}O$—⟨O⟩—COS—⟨O⟩—$OCH_2\overset{*}{C}HC_2H_5$ with $CH_3$ branch | 15 |
| 13 | $C_{10}H_{21}O$—⟨O⟩—COS—⟨O⟩—$OCH_2\overset{*}{C}HC_2H_5$ with $CH_3$ branch | 15 |
| 17 | $C_8H_{17}O$—$\overset{*}{C}HCH_2O$—⟨O⟩—COO—⟨O⟩—⟨O⟩—$COOC_6H_{13}$ with $CH_3$ branch | 25 |

-continued

| Ex. Compound No. | Structural formula | Wt. parts |
|---|---|---|
| 18 | 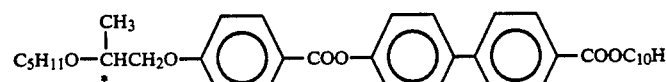 | 25 |
| 67 | 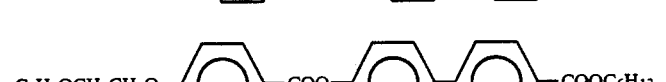 | 10 |
| 57 | 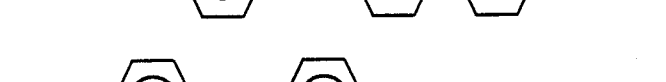 | 5 |
| 60 |  | 5 |

A liquid crystal composition 1-B was prepared by mixing the following Example compounds Nos. 1-18 and 2-29 with the above prepared composition 1-A.

| Ex. Comp. No. | Structural formula | Wt. parts |
|---|---|---|
| 1-18 | 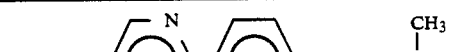 | 8 |
| 2-29 |  | 10 |
| Composition 1-A | | 82 |

The above-prepared liquid crystal composition 1-B was used to prepare a liquid crystal device in combination with a blank cell prepared in the following manner.

Two 1.1 mm-thick glass plates were provided and respectively coated with an ITO film to form an electrode for voltage application, which was further coated with an insulating layer of vapor-deposited $SiO_2$. The insulating layer was further coated with a 1.0 %-solution of polyimide resin precursor (SP-510, available from Toray K. K.) in dimethylacetoamide by a spinner coater rotating at 3000 rpm for 15 seconds. Thereafter, the coating film was subjected to heat curing at 300° C. for 60 min. to obtain about 120 Å-thick film. The coating film was rubbed with acetate fiber-planted cloth. The thus treated two glass plates were washed with isopropyl alcohol. After silica beads with an average particle size of 1.5 microns were dispersed on one of the glass plates, the two glass plates were applied to each other with a bonding sealing agent (Lixon Bond, available from Chisso K. K.) so that their rubbed directions were parallel to each other and heated at 100 ° C. for 60 min. to form a blank cell. The cell gap was found to be about 1.5 microns as measured by a Berek compensator.

Then, the above-prepared liquid crystal composition 1-B was heated into an isotropic liquid, and injected into the above prepared cell under vacuum and, after sealing, was gradually cooled at a rate of 20° C./hour to 25° C. to prepare a ferroelectric liquid crystal device.

Figure 4A:
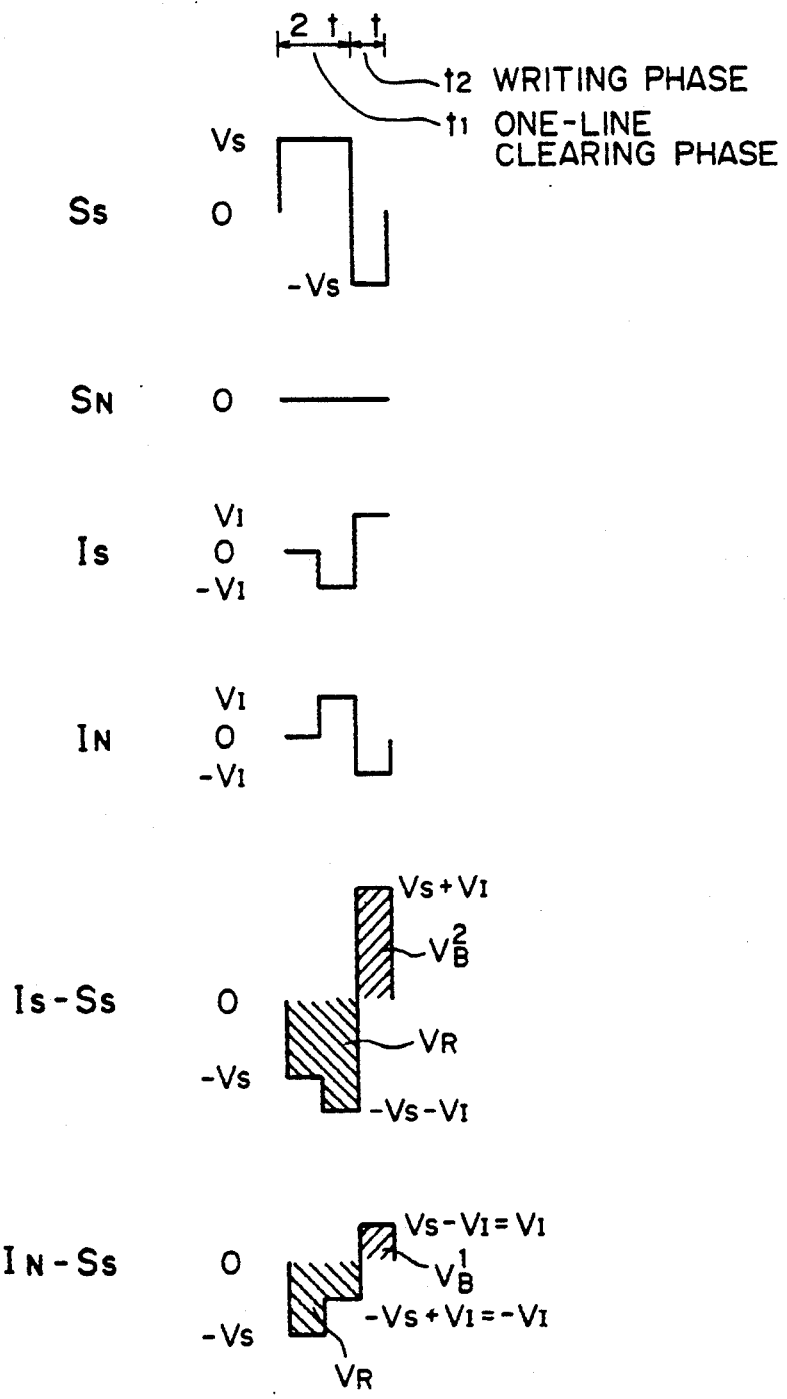
FIG. 4A shows unit driving waveforms used in an embodiment of the present invention.
Figure 4B:
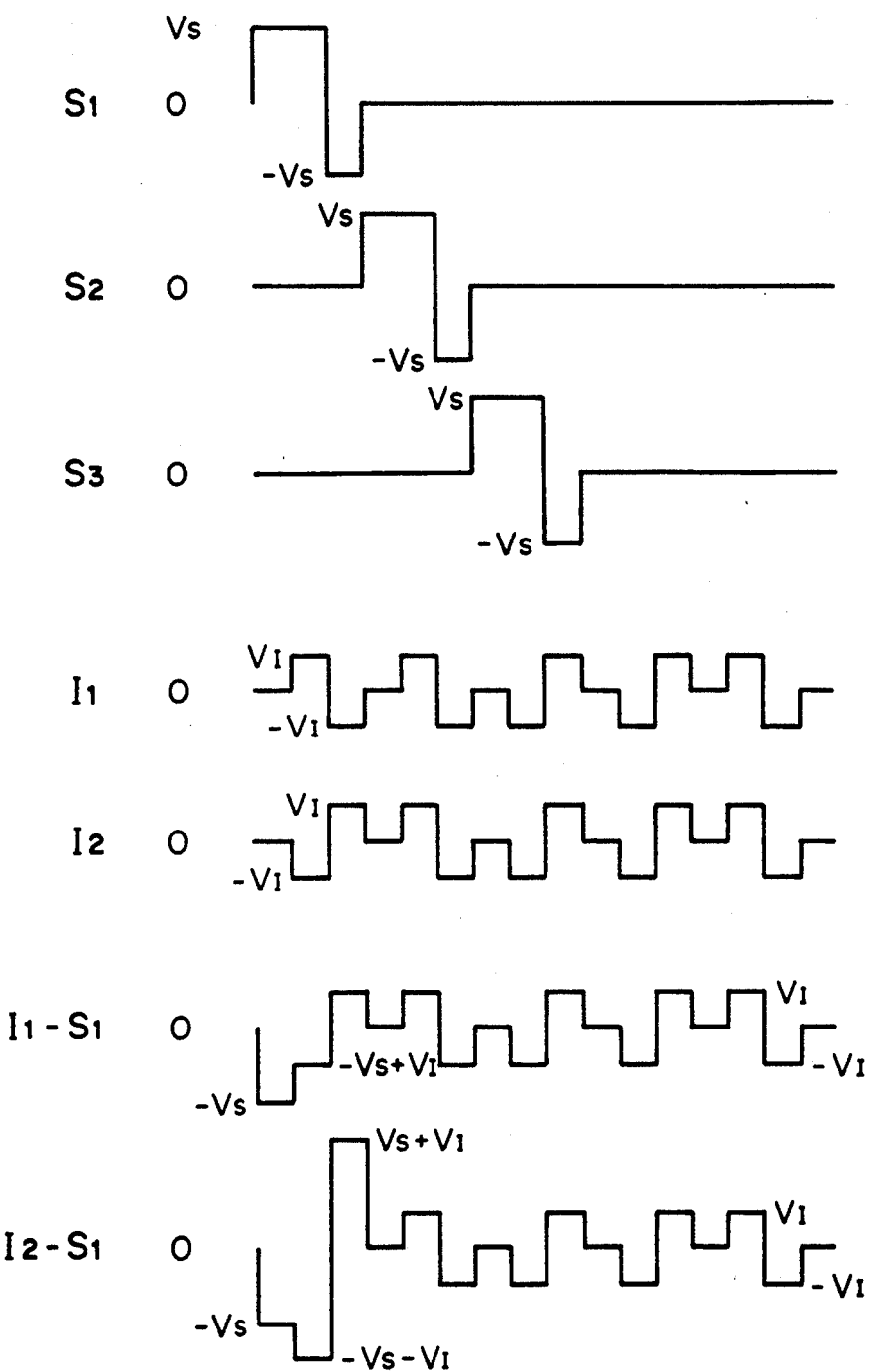
FIG. 4B is time-serial waveforms comprising a succession of such unit waveforms.
Figure 5:
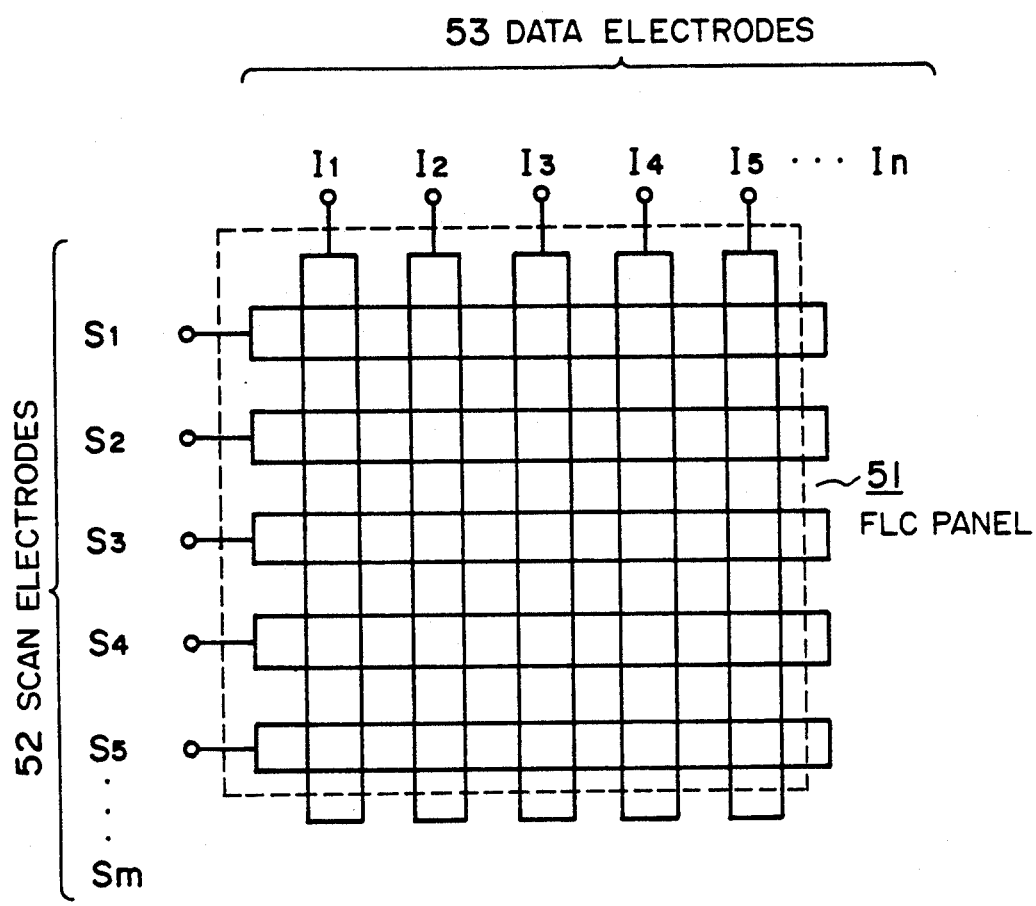
FIG. 5 is a plan view of a ferroelectric liquid crystal panel having a matrix electrode structure.
Figure 6:
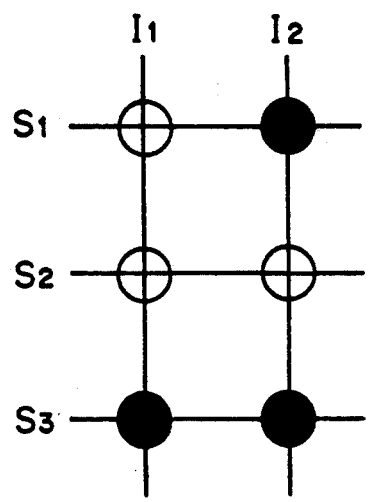
FIG. 6 is an illustration of a display pattern obtained by an actual drive using the time-serial waveforms shown in FIG. 4B.
Figure 7:
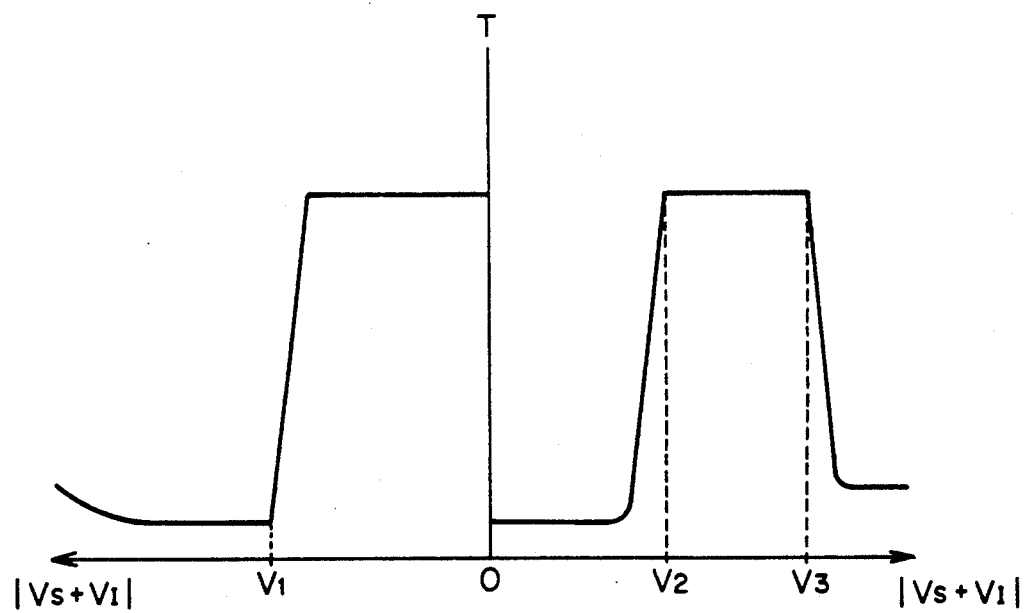
FIG. 7 is a V-T characteristic chart showing a change in transmittance under application of varying drive voltages.
Figure 8:
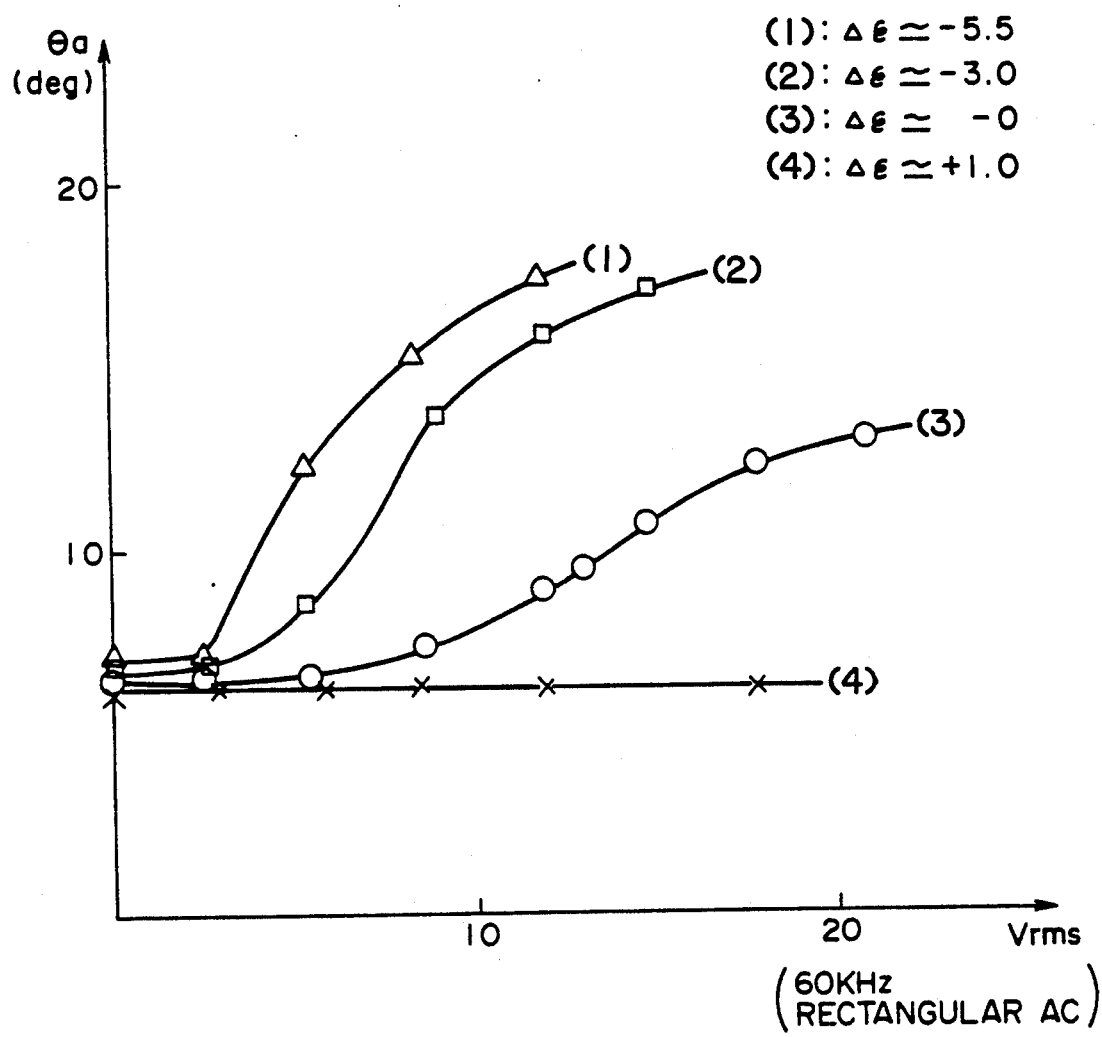
FIG. 8 is a graph showing changes in tilt angle θa versus effective voltage Vrms with respect to several ferroelectric liquid crystals having different values of dielectric anisotropy Δε.

The ferroelectric liquid crystal device was subjected to measurement of a driving voltage margin $\Delta V$ ($=V_3-V_1$) by using the driving waveforms (bias ratio$=\frac{1}{3}$) described with reference to FIGS. 4A and 4B and setting $\Delta t$ so as to provide $V_1$ of about 15 volts. The results are shown below.

| | 10° C. | 25° C. | 40° C. |
|---|---|---|---|
| Voltage margin $\Delta V$ (set $\Delta t$) | 12.5 V (950 μsec) | 12.5 V (280 μsec) | 9.0 V (100 μsec) |

Further, when the temperature was changed while the voltage ($V_S+V_I$) was set at a central value within the voltage margin, the temperature difference capable of driving (hereinafter called "(driving) temperature margin") was ±3.1° C.

Further, a contrast of 8 was attained at 25° C. during the driving.

COMPARATIVE EXAMPLE 1

A liquid crystal composition 1-C was prepared by omitting Example compound No. 2-29 from the liquid crystal composition 1-B, i.e., by adding only Example compound No. 1-18 to the liquid crystal composition 1-A, and a liquid crystal composition 1-D was prepared by omitting Example compound No. 1-18 from the composition 1-B, i.e., by adding only Example compound No. 2-29 to the composition 1-A.

Ferroelectric liquid crystal devices 1-A, 1-C and 1-D were prepared by using the compositions 1-A, 1-C and 1-D, respectively, instead of the composition 1-B, and subjected to measurement of driving voltage margin ΔV, otherwise in the same manner as in Example 1. The results are shown below.

|     | Voltage margin ΔV (set Δt) | | |
| --- | --- | --- | --- |
|     | 10° C. | 25° C. | 40° C. |
| 1-A | 10.0 V | 10.0 V | 8.0 V |
|     | (1300 μsec) | (340 μsec) | (100 μsec) |
| 1-C | 10.5 V | 11.0 V | 8.0 V |
|     | (1100 μsec) | (310 μsec) | (100 μsec) |
| 1-D | 11.0 V | 11.0 V | 9.0 V |
|     | (1100 μsec) | (310 μsec) | (100 μsec) |

Further, the driving temperature margin with respect to 25° C. was ±2.4° C. for 1-A, ±2.6° C. for 1-C and +2.7° C. for 1-D.

As apparent from the above Example 1 and Comparative Example 1, the ferroelectric liquid crystal device containing the liquid crystal composition 1-B according to the present invention provided wider driving voltage and temperature margins and showed a better performance of retaining good images in resistance to changes in environmental temperature and cell gap.

EXAMPLE 2

A liquid crystal composition 2-B was prepared by mixing the following example compounds in the indicated proportions with the liquid crystal composition 1-A prepared in Example 1.

| Ex. Comp. No. | Structural formula | Wt. parts |
| --- | --- | --- |
| 1-13 | n-$C_{12}H_{25}$—[pyrimidine]—[phenyl]—O$(CH_2)_4$$\overset{*}{C}H$($CH_3$)$C_2H_5$ | 7 |
| 1-37 | n-$C_{12}H_{25}$—[pyrimidine]—[phenyl]—O$(CH_2)_4$OCH$_2$$\overset{*}{C}H$($CH_3$)$C_2H_5$ | 3 |
| 2-12 | n-$C_5H_{11}$—[pyrimidine]—[phenyl]—[phenyl]—$C_6H_{13}$-n | 15 |
| Composition 1-A | | 75 |

A ferroelectric liquid crystal device was prepared in the same manner as in Example 1 except that the above liquid crystal composition 2-B was used, and the device was subjected to measurement of driving voltage margin and observation of switching states. In the device, a monodomain with a good and uniform alignment characteristic was observed. The results of the measurement are shown below.

|                | 10° C. | 25° C. | 40° C. |
| --- | --- | --- | --- |
| Voltage margin | 13.0 V | 13.5 V | 10.0 V |
| (set Δt)       | (850 μsec) | (260 μsec) | (100 μsec) |

Further, the driving temperature margin with respect to 25° C. was ±3.8° C. A contrast of 9 was attained during the drive at the temperature.

COMPARATIVE EXAMPLE 2

A liquid crystal composition 2-C was prepared by omitting Example compound No. 2-12 from the liquid crystal composition 2-B, i.e., by adding only Example compounds Nos. 1-13 and 1-37 to the liquid crystal composition 1-A, and a liquid crystal composition 2-D was prepared by omitting Example compounds Nos. 1-13 and 1-37 from the composition 2-B, i.e., by adding only Example compound No. 2-12 to the composition 1-A.

Ferroelectric liquid crystal devices 1-A, 2-C and 2-D were prepared by using the compositions 1-A, 2-C and 2-D, respectively, instead of the composition 1-B, and subjected to measurement of driving voltage margin ΔV, otherwise in the same manner as in Example 1. The results are shown below.

|     | Voltage margin ΔV (set Δt) | | |
| --- | --- | --- | --- |
|     | 10° C. | 25° C. | 40° C. |
| 1-A | 10.0 V | 10.0 V | 8.0 V |
|     | (1300 μsec) | (340 μsec) | (100 μsec) |
| 2-C | 10.0 V | 11.0 V | 8.5 V |
|     | (1100 μsec) | (300 μsec) | (100 μsec) |
| 2-D | 11.0 V | 11.5 V | 9.5 V |

Further, the driving temperature margin with respect to 25° C. was ±2.4° C. for 1-A, ± 2.7° C. for 2-C and ±2.9° C. for 2-D.

As apparent from the above Example 2 and Comparative Example 2, the ferroelectric liquid crystal device containing the liquid crystal composition 2-B according to the present invention provided wider driving voltage and temperature margins and showed a better performance of retaining good images in resistance to changes in environmental temperature and cell gap.

EXAMPLE 3

A liquid crystal composition 3-B was prepared by mixing the following example compounds in the indicated proportions with the liquid crystal composition 1-A prepared in Example 1.

| Ex. Comp. No. | Structural formula | wt. parts |
|---|---|---|
| 1-16 | n-C$_8$H$_{17}$—[N=N phenyl]—[phenyl]—O(CH$_2$)$_3$CH(CH$_3$)C$_2$H$_5$* | 8 |
| 2-11 | n-C$_7$H$_{15}$—[N=N phenyl]—[phenyl]—[phenyl]—C$_6$H$_{13}$-n | 10 |
| 2-44 | n-C$_{10}$H$_{21}$—[phenyl]—[N=N phenyl]—[phenyl]—OCH$_2$CH(CH$_3$)C$_2$H$_5$* | 4 |
| Composition 1-A | | 78 |

A ferroelectric liquid crystal device was prepared in the same manner as in Example 1 except that the above liquid crystal composition 3-B was used, and the device was subjected to measurement of driving voltage margin and observation of switching states. In the device, a monodomain with a good and uniform alignment characteristic was observed. The results of the measurement are shown below.

|  | 10° C. | 25° C. | 40° C. |
|---|---|---|---|
| Voltage margin (set Δt) | 12.5 V (850 μsec) | 12.5 V (260 μsec) | 9.0 V (100 μsec) |

Further, the driving temperature margin with respect to 25° C. was ±3.5° C. A contrast of 10 was attained during the drive at the temperature.

COMPARATIVE EXAMPLE 3

A liquid crystal composition 3-C was prepared by omitting Example compounds Nos. 2-11 and 2-44 from the liquid crystal composition 3-B, i.e., by adding only Example compound No. 1-16 to the liquid crystal composition 1-A, and a liquid crystal composition 3-D was prepared by omitting Example compound No. 1-16 from the composition 3-B, i.e., by adding only Example compounds Nos. 2-11 and 2-44 to the composition 1-A.

Ferroelectric liquid crystal devices 1-A, 3-C and 3-D were prepared by using the compositions 1-A, 3-C and 3-D, respectively, instead of the composition 1-B, and subjected to measurement of driving voltage margin ΔV, otherwise in the same manner as in Example 1. The results are shown below.

|  | Voltage margin ΔV (set Δt) | | |
|---|---|---|---|
|  | 10° C. | 25° C. | 40° C. |
| 1-A | 10.0 V (1300 μsec) | 10.0 V (340 μsec) | 8.0 V (100 μsec) |
| 3-C | 10.5 V (1100 μsec) | 11.0 V (310 μsec) | 8.5 V (100 μsec) |
| 3-D | 11.0 V (1100 μsec) | 11.5 V (310 μsec) | 9.0 V (100 μsec) |

Further, the driving temperature margin with respect to 25° C. was ±2.4° C. for 1-A, ±2.5° C. for 3-C and ±2.8° C. for 3-D.

As apparent from the above Example 3 and Comparative Example 3, the ferroelectric liquid crystal device containing the liquid crystal composition 3-B according to the present invention provided wider driving voltage and temperature margins and showed a better performance of retaining good images in resistance to changes in environmental temperature and cell gap.

EXAMPLE 4

A liquid crystal composition 4-A was prepared by mixing the following compounds in respectively indicated proportions.

| Ex. Compound No. | Structural formula | Wt. parts |
|---|---|---|
| 24 | C$_{10}$H$_{21}$O—[phenyl]—COS—[phenyl]—OCH$_2$CH(CH$_3$)OC$_3$H$_7$* | 15 |
| 25 | C$_{12}$H$_{25}$O—[phenyl]—COS—[phenyl]—OCH$_2$CH(CH$_3$)OC$_8$H$_{17}$* | 15 |

-continued

| Ex. Compound No. | Structural formula | Wt. parts |
|---|---|---|
| 67 | C₄H₉OCH₂CH₂O—⌬—COO—⌬—⌬—COOC₆H₁₃ | 15 |
| 4 | C₂H₅CH(CH₃)CH₂—⌬—⌬—COO—⌬—OC₈H₁₇ | 8 |
| 5 | C₂H₅CH(CH₃)CH₂—⌬—⌬—COO—⌬—OC₆H₁₃ | 20 |
| 57 | C₁₀H₂₁O—⌬—COO—⌬—OC₈H₁₇ | 10 |
| 58 | C₈H₁₇—⌬—COO—⌬—OC₁₀H₂₁ | 15 |
| 47 | C₁₀H₂₁O—⌬—⌬—COO—⌬—OCH₂CHFC₈H₁₇ | 8 |

A liquid crystal composition 4-B was prepared by mixing the following Example compounds Nos. 1-14, 1-25, 2-5 and 2-8 with the above prepared composition 6-A.

| Ex. Comp. No. | Structural formula | wt. parts |
|---|---|---|
| 1-14 | n-C₆H₁₃—(pyrimidine)—⌬—O(CH₂)₃CH(CH₃)C₂H₅ | 7 |
| 1-25 | n-C₁₁H₂₃—(pyrimidine)—⌬—O—C(=O)(CH₂)₂CH(CH₃)C₂H₅ | 4 |
| 2-5 | n-C₃H₇—(pyrimidine)—⌬—⌬—OC₁₁H₂₃-n | 7 |
| 2-8 | n-C₈H₁₇—(pyrimidine)—⌬—⌬—OC(=O)—C₆H₁₃-n | 6 |
| Composition 4-A | | 76 |

A ferroelectric liquid crystal device 4-B was prepared in the same manner as in Example 1 except that the liquid crystal composition 4-B was used instead of the composition 1-B. The device was subjected to measurement of driving voltage margin and observation of switching states. In the device, a monodomain with a good and uniform alignment characteristic was observed. The results of the measurement are shown below.

| | 5° C. | 25° C. | 45° C. |
|---|---|---|---|
| Voltage margin (set Δt) | 11.0 V (450 μsec) | 12.7 V (105 μsec) | 8.5 V (40 μsec) |

Further, the driving temperature margin with respect to 25° C. was ±3.0° C. A contrast of 9 was attained during the drive at the temperature.

COMPARATIVE EXAMPLE 4

A liquid crystal composition 4-C was prepared by omitting Example compounds Nos. 2-5 and 2-8 from the liquid crystal composition 4-B prepared in Example 4, mance of retaining good images in resistance to changes in environmental temperature and cell gap.

EXAMPLE 5

A liquid crystal composition 5-B was prepared by mixing the following example compounds in the indicated proportions with the liquid crystal composition 4-A prepared in Example 4.

| Ex. Comp. No. | Structural formula | wt. parts |
|---|---|---|
| 1-16 | 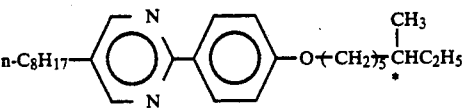 | 6 |
| 1-2 | 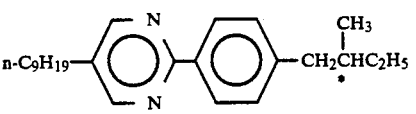 | 2 |
| 2-14 | 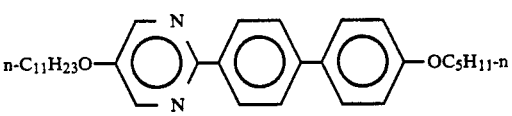 | 6 |
| 2-50 | 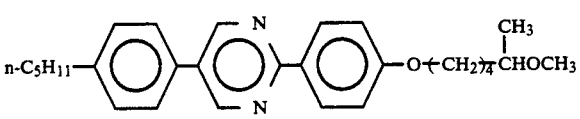 | 3 |
| 2-11 | 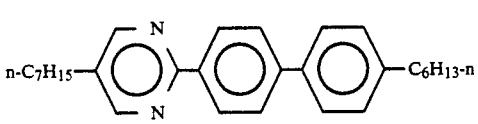 | 5 |
| Composition 4-A | | 78 | i.e., by adding only Example compounds Nos. 1-14 and 1-25 to the liquid crystal composition 4-A, and a liquid crystal composition 4-D was prepared by omitting Example compounds Nos. 1-14 and 1-25 from the composition 4-B, i.e., by adding only Example compounds Nos. 2-5 and 2-8 to the composition 4-A.

Ferroelectric liquid crystal devices 4-A, 4-C and 4-D were prepared by using the compositions 4-A, 4-C and 4-D, respectively, instead of the composition 1-B, and subjected to measurement of driving voltage margin $\Delta V$, otherwise in the same manner as in Example 1. The results are shown below.

|  | Voltage margin $\Delta V$ (set $\Delta t$) | | |
|---|---|---|---|
|  | 10° C. | 25° C. | 40° C. |
| 4-A | 7.0 V | 9.0 V | 6.0 V |
|  | (525 μsec) | (140 μsec) | (45 μsec) |
| 4-C | 7.5 V | 9.5 V | 6.0 V |
|  | (520 μsec) | (130 μsec) | (45 μsec) |
| 4-D | 8.0 V | 10.0 V | 7.0 V |
|  | (505 μsec) | (120 μsec) | (45 μsec) |

Further, the driving temperature margin with respect to 25° C. was ±2.0° C. for 4-A, ±2.1° C. for 4-C and ±2.3° C. for 4-D.

As apparent from the above Example 4 and Comparative Example 4, the ferroelectric liquid crystal device containing the liquid crystal composition 4-B according to the present invention provided wider driving voltage and temperature margins and showed a better perfor- A ferroelectric liquid crystal device was prepared in the same manner as in Example 1 except that the above liquid crystal composition 5-B was used, and the device was subjected to measurement of driving voltage margin and observation of switching states. In the device, a monodomain with a good and uniform alignment characteristic was observed. The results of the measurement are shown below.

|  | 10° C. | 25° C. | 40° C. |
|---|---|---|---|
| Voltage margin (set $\Delta t$) | 11.0 V (450 μsec) | 12.5 V (110 μsec) | 8.0 V (40 μsec) |

Further, the driving temperature margin with respect to 25° C. was ±3.0° C. A contrast of 10 was attained during the drive at the temperature.

COMPARATIVE EXAMPLE 5

A liquid crystal composition 5-C was prepared by omitting Example compounds Nos. 2-14, 2-50 and 2-11 from the liquid crystal composition 5-B, i.e., by adding only Example compounds Nos. 1-16 and 1-2 to the liquid crystal composition 4-A, and a liquid crystal composition 5-D was prepared by omitting Example compounds Nos. 1-16 and 1-2 from the composition 5-B, i.e., by adding only Example compounds Nos. 2-14, 2-50 and 2-11 to the composition 4-A.

Ferroelectric liquid crystal devices 4-A, 5-C and 5-D were prepared by using the compositions 4-A, 5-C and 5-D, respectively, instead of the composition 1-B, and subjected to measurement of driving voltage margin ΔV, otherwise in the same manner as in Example 1. The results are shown below.

|  | Voltage margin ΔV (set Δt) | | |
|---|---|---|---|
|  | 10° C. | 25° C. | 40° C. |
| 4-A | 7 V | 9 V | 6 V |
|  | (525 μsec) | (140 μsec) | (45 μsec) |
| 5-C | 7.5 V | 9 V | 6.5 V |
|  | (480 μsec) | (120 μsec) | (45 μsec) |
| 5-D | 8.0 V | 10 V | 7.0 V |
|  | (510 μsec) | (115 μsec) | (45 μsec) |

Further, the driving temperature margin with respect to 25° C. was ±2.0° C. for 4-A, ±2.2° C. for 5-C and ±2.4° C. for 5-D.

As apparent from the above Example 5 and Comparative Example 5, the ferroelectric liquid crystal device containing the liquid crystal composition 5-B according to the present invention provided wider driving voltage and temperature margins and showed a better performance of retaining good images in resistance to changes in environmental temperature and cell gap.

EXAMPLE 6

A liquid crystal composition 6-A was prepared by mixing the following compounds in respectively indicated proportions.

| Ex. Compound No. | Structural formula | wt. parts |
|---|---|---|
| 8 | 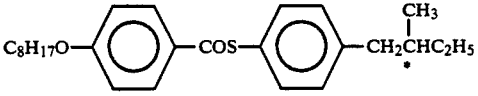 C$_8$H$_{17}$O—〈ph〉—COS—〈ph〉—CH$_2$CH(CH$_3$)C$_2$H$_5$ * | 45 |
| 9 | C$_{12}$H$_{25}$O—〈ph〉—COS—〈ph〉—CH$_2$CH(CH$_3$)C$_2$H$_5$ * | 45 |
| 12 | C$_8$H$_{17}$O—〈ph〉—COS—〈ph〉—OCH$_2$CH(CH$_3$)C$_2$H$_5$ * | 15 |
| 13 | C$_{10}$H$_{21}$O—〈ph〉—COS—〈ph〉—OCH$_2$CH(CH$_3$)C$_2$H$_5$ * | 15 |
| 17 | C$_8$H$_{17}$O—CH(CH$_3$)CH$_2$O—〈ph〉—COO—〈ph〉—〈ph〉—COOC$_6$H$_{13}$ * | 30 |
| 18 | C$_5$H$_{11}$O—CH(CH$_3$)CH$_2$O—〈ph〉—COO—〈ph〉—〈ph〉—COOC$_{10}$H$_{21}$ * | 30 |
| 67 | C$_4$H$_9$OCH$_2$CH$_2$O—〈ph〉—COO—〈ph〉—〈ph〉—COOC$_6$H$_{13}$ | 10 |

A liquid crystal composition 6-B was prepared by mixing the following Example compounds Nos. 1-16, 2-11, and 2-44 with the above prepared composition 6-A.

| Ex. Comp. No. | Structural formula | Wt. parts |
|---|---|---|
| 1-16 | 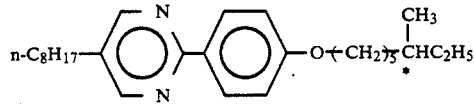 n-C$_8$H$_{17}$—〈pyrimidine〉—〈ph〉—O(CH$_2$)$_3$CH(CH$_3$)C$_2$H$_5$ * | 12 |

-continued

| Ex. Comp. No. | Structural formula | Wt. parts |
|---|---|---|
| 2-11 | n-C$_7$H$_{15}$—[pyrimidine]—[phenyl]—[phenyl]—C$_6$H$_{13}$-n | 15 |
| 2-44 | n-C$_{10}$H$_{21}$—[phenyl]—[pyrimidine]—[phenyl]—OCH$_2$CHC$_2$H$_5$ (CH$_3$) | 6 |
| Composition 6-A | | 80 |

A ferroelectric liquid crystal device 6-B was prepared in the same manner as in Example 1 except that the liquid crystal composition 6-B was used instead of the composition 1-B. The device was subjected to measurement of driving voltage margin and observation of switching states. In the device, a monodomain with a good and uniform alignment characteristic was observed. The results of the measurement are shown below.

| | 10° C. | 25° C. | 45° C. |
|---|---|---|---|
| Voltage margin (set Δt) | 13.5 V (700 μsec) | 14 V (220 μsec) | 11.0 V (75 μsec) |

Further, the driving temperature margin with respect to 25° C. was ±4.0° C. A contrast of 11 was attained during the drive at the temperature.

COMPARATIVE EXAMPLE 6

A liquid crystal composition 6-C was prepared by omitting Example compounds Nos. 2-11 and 2-44 from the liquid crystal composition 6-B, i.e., by adding only Example compound No. 1-16 to the liquid crystal composition 6-A, and a liquid crystal composition 6-D was prepared by omitting Example compound No. 1-16 from the composition 6-B, i.e., by adding only Example compounds Nos. 2-11 and 2-44 to the composition 6-A.

Ferroelectric liquid crystal devices 6-A, 6-C and 6-D were prepared by using the compositions 6-A, 6-C and 6-D, respectively, instead of the composition 1-B, and subjected to measurement of driving voltage margin ΔV, otherwise in the same manner as in Example 1. The results are shown below.

| | Voltage margin ΔV (set Δt) | | |
|---|---|---|---|
| | 10° C. | 25° C. | 40° C. |
| 6-A | 9 V (1050 μsec) | 9.5 V (280 μsec) | 8.5 V (78 μsec) |
| 6-C | 10.5 V (900 μsec) | 11.0 V (250 μsec) | 9.0 V (78 μsec) |
| 6-D | 11.0 V (900 μsec) | 11.0 V (250 μsec) | 9.5 V (78 μsec) |

Further, the driving temperature margin with respect to 25° C. was ±2.2° C. for 6-A, ±2.6° C. for 6-C and ±2.6° C. for 6-D.

As apparent from the above Example 6 and Comparative Example 6, the ferroelectric liquid crystal device containing the liquid crystal composition 6-B according to the present invention provided wider driving voltage and temperature margins and showed a better performance of retaining good images in resistance to changes in environmental temperature and cell gap.

EXAMPLE 7

A liquid crystal composition 7-B was prepared by mixing the following example compounds in the indicated proportions with the liquid crystal composition 6-A prepared in Example 6.

| Ex. Comp. No. | Structural formula | wt. parts |
|---|---|---|
| 1-6 | n-C$_{12}$H$_{25}$—[pyrimidine]—[phenyl]—O(CH$_2$)$_2$CHC$_2$H$_5$ (CH$_3$) * | 8 |
| 2-10 | n-C$_8$H$_{17}$—[pyrimidine]—[phenyl]—[phenyl]—C$_5$H$_{11}$-n | 6 |
| 2-32 | n-C$_4$H$_9$—[phenyl]—[pyrimidine]—[phenyl]—C$_7$H$_{15}$-n | 2 |
| Composition 6-A | | 84 |

A ferroelectric liquid crystal device was prepared in the same manner as in Example 1 except that the above liquid crystal composition 7-B was used, and the device was subjected to measurement of driving voltage margin and observation of switching states. In the device, a monodomain with a good and uniform alignment characteristic was observed. The results of the measurement are shown below.

|  | 10° C. | 25° C. | 40° C. |
|---|---|---|---|
| Voltage margin (set Δt) | 12.0 V (720 μsec) | 12.3 V (210 μsec) | 9.5 V (80 μsec) |

Further, the driving temperature margin with respect to 25° C. was ±3.0° C. A contrast of 10 was attained during the drive at the temperature.

COMPARATIVE EXAMPLE 7

A liquid crystal composition 7-C was prepared by omitting Example compounds Nos. 2-10 and 2-32 from the liquid crystal composition 7-B, i.e., by adding only Example compound No. 1-6 to the liquid crystal composition 6-A, and a liquid crystal composition 7-D was prepared by omitting Example compound No. 1-6 from the composition 7-B, i.e., by adding only Example compounds Nos. 2-10 and 2-32 to the composition 6-A.

Ferroelectric liquid crystal devices 6-A, 7-C and 7-D were prepared by using the compositions 6-A, 7-C and 7-D, respectively, instead of the composition 1-B, and subjected to measurement of driving voltage margin ΔV, otherwise in the same manner as in Example 1. The results are shown below.

|  | Voltage margin ΔV (set Δt) | | |
|---|---|---|---|
|  | 10° C. | 25° C. | 40° C. |
| 6-A | 9 V (1050 μsec) | 9.5 V (280 μsec) | 8.5 V (78 μsec) |
| 7-C | 10.0 V (900 μsec) | 9.5 V (250 μsec) | 8.5 V (78 μsec) |
| 7-D | 10.5 V (900 μsec) | 10.0 V (250 μsec) | 8.5 V (78 μsec) |

Further, the driving temperature margin with respect to 25° C. was ±2.2° C. for 6-A, ±2.2° C. for 7-C and ±2.5° C. for 7-D.

As apparent from the above Example 7 and Comparative Example 7, the ferroelectric liquid crystal device containing the liquid crystal composition 7-B according to the present invention provided wider driving voltage and temperature margins and showed a better performance of retaining good images in resistance to changes in environmental temperature and cell gap.

EXAMPLE 8

A blank cell was prepared in the same manner as in Example 1 except for omitting the $SiO_2$ layer to form an alignment control layer composed of the polyimide resin layer alone on each electrode plate. Four ferroelectric liquid crystal devices were prepared by filling such a blank cell with liquid crystal compositions 6-B, 6-C, 6-D and 6-A, respectively, prepared in Example 6 and Comparative Example 6. These liquid crystal devices were subjected to measurement of driving voltage and temperature margins in the same manner as in Example 1. The results are shown below.

| Comp. | Voltage margin (set Δt) | | | Temp. margin (at 25° C.) |
|---|---|---|---|---|
|  | 10° C. | 25° C. | 40° C. |  |
| 6-B | 13.5 V (700 μsec) | 14.0 V (220 μsec) | 11.5 V (75 μsec) | ±4.0° C. |
| 6-C | 11.0 V (850 μsec) | 11.0 V (250 μsec) | 9.5 V (75 μsec) | ±2.7° C. |
| 6-D | 11.5 V (850 μsec) | 11.5 V (250 μsec) | 9.5 V (75 μsec) | ±2.7° C. |
| 6-A | 9.5 V (950 μsec) | 10.0 V (250 μsec) | 9.0 V (75 μsec) | ±2.4° C. |

As is apparent from the above Example 8, also in the case of a different device structure, the device containing the ferroelectric liquid crystal composition 6-B according to the present invention provided wider driving voltage and temperature margins and showed a better performance of retaining good images in resistance to changes in environmental temperature and cell gap than the device containing the other liquid crystal compositions.

EXAMPLES 9–16

Liquid crystal compositions 9-B to 16-B were prepared by replacing the example compounds and the liquid crystal compositions used in Example 1, 4 and 6 with example compounds and liquid crystal compositions shown in the following Table 1. Ferroelectric liquid crystal devices were prepared by respectively using these compositions instead of the composition 1-B, and subjected to measurement of driving margins and observation of switching states. In the devices, a monodomain with a good and uniform alignment characteristic was observed. The results of the measurement are shown in the following Table 1.

TABLE 1

| Ex. No. (Comp. No.) | Example compound No. or liquid crystal composition No. (weight parts) | | | | | | | | Voltage margin (V) Set Δt (μsec) | Temp. margin (°C.) |
|---|---|---|---|---|---|---|---|---|---|---|
| 9 | 1-3 | 1-6 | 1-14 |  | 2-12 | 2-19 | 2-32 |  | 1-A | 13.0 | ±3.3 |
| (9-B) | (4) | (4) | (6) |  | (6) | (6) | (4) |  | (70) | 220 |  |
| 10 | 1-16 | 1-18 | 1-29 | 1-37 | 2-6 | 2-10 | 2-46 |  | 1-A | 12.5 | ±3.1 |
| (10-B) | (5) | (5) | (3) | (3) | (3) | (5) | (2) |  | (74) | 270 |  |
| 11 | 1-13 | 1-18 | 1-25 |  | 2-5 | 2-12 | 2-39 |  | 4-A | 12.0 | ±2.8 |
| (11-B) | (8) | (4) | (4) |  | (3) | (6) | (2) |  | (73) | 110 |  |
| 12 | 1-6 | 1-17 | 1-20 |  | 2-8 | 2-29 | 2-36 | 2-46 | 4-A | 12.0 | ±2.8 |
| (12-B) | (5) | (8) | (2) |  | (2) | (5) | (2) | (2) | (74) | 110 |  |
| 13 | 1-10 | 1-22 | 1-35 | 1-40 | 2-11 | 2-32 | 2-41 | 2-56 | 4-A | 12.5 | ±2.9 |
| (13-B) | (5) | (3) | (3) | (3) | (6) | (3) | (3) | (3) | (71) | 130 |  |
| 14 | 1-2 | 1-15 | 1-26 | 1-32 | 2-4 | 2-10 | 2-12 | 2-24 | 6-A | 13.0 | ±3.3 |
| (14-B) | (4) | (2) | (4) | (3) | (2) | (5) | (4) | (2) | (73) | 220 |  |
| 15 | 1-16 | 1-17 | 1-37 |  | 2-9 | 2-11 | 2-12 | 2-44 | 6-A | 13.0 | ±3.2 |
| (15-B) | (5) | (3) | (3) |  | (3) | (4) | (4) | (3) | (75) | 220 |  |
| 16 | 1-14 | 1-19 | 1-40 |  | 2-10 | 2-19 | 2-44 |  | 6-A | 12.5 | ±3.0 |

TABLE 1-continued

| Ex. No. (Comp. No.) | Example compound No. or liquid crystal composition No. (weight parts) | | | | | | Voltage margin (V) Set Δt (μsec) | Temp. margin (°C.) |
|---|---|---|---|---|---|---|---|---|
| (16-B) | (6) | (4) | (2) | (5) | (3) | (2) | (78) | 250 |

As is apparent from the results shown in the above Table 1, the ferroelectric liquid crystal devices containing the liquid crystal compositions 9-B to 16-B provided wide driving voltage and temperature margins and showed good performances of retaining good images in resistance to changes in environmental temperature and cell gap.

EXAMPLE 17

A liquid crystal composition 17-B was prepared by mixing the following example compound in the indicated proportion with the liquid crystal composition 1-B prepared in Example 1.

| Ex. Comp. No. | Structural formula | wt. parts |
|---|---|---|
| 3-10 | n-$C_5H_{11}$—(H)—CO—(⌬)—$OC_6H_{13}$-n with CN, CN substituents | 10 |
| | Composition 1-B | 90 |

A ferroelectric liquid crystal device was prepared in the same manner as in Example 1 except that the above liquid crystal composition was used, and the device was subjected to measurement of driving voltage margin in the same manner as in Example 1 to obtain the following results.

| | 10° C. | 25° C. | 40° C. |
|---|---|---|---|
| Voltage margin (set Δt) | 12.5 V (1050 μsec) | 12.5 V (315 μsec) | 9.0 V (110 μsec) |

Then, the tilt angle of the above device was measured under right-angle cross nicols at 25° C. to provide 7.6 degrees. Further, the tilt angle of the device was again measured while being subjected to application of rectangular waveforms of ±8 V and a frequency of 60 KHz and found to be 13 degrees. The transmittance measured at that time was 12.5%, and a contrast of 55:1 was attained.

COMPARATIVE EXAMPLE 17

A liquid crystal composition 17-C was prepared in the same manner as in Example 17 except that the liquid crystal composition 1-A prepared in Example 1 was used instead of the composition 1-B to be mixed with the Example compound No. 3-10 in the same proportions.

Ferroelectric liquid crystal devices were prepared by using the compositions 17-C, 1-A and 1-B respectively and subjected to measurement of driving voltage margin, otherwise in the same manner as in Example 1. Further, the tilt angles of these devices were measured in the same manner as in Example 17. The results are shown below.

| | Voltage margin (set Δt) | | |
|---|---|---|---|
| Comp. | 10° C. | 25° C. | 40° C. |
| 1-A | 10 V (1300 μsec) | 10 V (340 μsec) | 8.0 V (100 μsec) |
| 1-B | 12.5 V (950 μsec) | 12.5 V (280 μsec) | 9.0 V (100 μsec) |
| 17-C | 10 V (1550 μsec) | 10 V (380 μsec) | 7.5 V (108 μsec) |

| | Tilt angle (25° C.) | |
|---|---|---|
| Comp. | Initial (no electric field) | Under AC appln. (60 KHz, ±8 V, rectangular) |
| 1-A | 7.9 degrees | 8.2 degrees |
| 1-B | 7.5 degrees | 7.7 degrees |
| 17-C | 7.8 degrees | 13.2 degrees |

As apparent from Example 17 and Comparative Example 17, the liquid crystal composition 17-B obtained by mixing a mesomorphic compound having a negative dielectric anisotropy (Example compound No. 3-10) with the liquid crystal composition 1-B according to the present invention provided a wider driving margin and also provided a remarkably improved display characteristic when used in a display method utilizing AC applicaton (or AC stabilization).

EXAMPLE 18

A liquid crystal composition 18-B was prepared by mixing the following example compounds in the respectively indicated proportions with the liquid crystal composition 1-B prepared in Example 1.

| Ex. Comp. No. | Structural formula | wt. parts |
|---|---|---|
| 3-90 | n-$C_{10}H_{21}$—(N=N thiadiazole)—(⌬)—$OC_{12}H_{25}$-n | 5 |
| 3-12 | n-$C_8H_{17}$—(H)—CO—(⌬)—$OC_8H_{17}$-n with CN, CN substituents | 5 |

-continued

| Ex. Comp. No. | Structural formula | wt. parts |
|---|---|---|
| 3-122 | n-C$_8$H$_{17}$—[H]—[H]—C$_8$H$_{17}$-n, with CN on second ring | 2 |
| 3-70 | n-C$_6$H$_{13}$—[⎔(N=N)]—[⎔]—OC$_5$H$_{11}$-n | 3 |
| 3-107 | n-C$_{10}$H$_{21}$—[N——N / S thiadiazole]—[⎔]—OC(=O)—[H]—C$_3$H$_7$-n | 3 |
| 3-111 | n-C$_{12}$H$_{25}$—[N——N / S thiadiazole]—[⎔]—OCH$_2$—[H]—C$_5$H$_{11}$-n | 1 |
| 3-167 | n-C$_9$H$_{19}$O—[⎔]—CH=C(CN)—[⎔]—C$_7$H$_{15}$-n | 1 |
| Composition 1-B | | 80 |

A ferroelectric liquid crystal device was prepared in the same manner as in Example 1 except that the above liquid crystal composition was used, and the device was subjected to measurement of driving voltage margin in the same manner as in Example 1 to obtain the following results.

|  | 10° C. | 25° C. | 40° C. |
|---|---|---|---|
| Voltage margin (set Δt) | 13 V (1030 μsec) | 12.5 V (310 μsec) | 9.5 V (105 μsec) |

Then, the tilt angle of the above device was measured under right-angle cross nicols at 25° C. to provide 8.4 degrees. Further, the tilt angle of the device was again measured while being subjected to application of rectangular waveforms of ±8 V and a frequency of 60 KHz and found to be 12.9 degrees. The transmittance measured at that time was 13%, and a contrast of 45:1 was attained.

COMPARATIVE EXAMPLE 18

A liquid crystal composition 18-C was prepared in the same manner as in Example 18 except that the liquid crystal composition 1-A prepared in Example 1 was used instead of the composition 1-B to be mixed with the other example compounds in the same proportions.

Ferroelectric liquid crystal devices were prepared by using the compositions 18-C, 1-A and 1-B respectively and subjected to measurement of driving voltage margin, otherwise in the same manner as in Example 1. Further, the tilt angles of these devices were measured in the same manner as in Example 21. The results are shown below.

|  | Voltage margin (set Δt) | | |
|---|---|---|---|
| Comp. | 10° C. | 25° C. | 40° C. |
| 1-A | 10 V (1300 μsec) | 10 V (340 μsec) | 8.0 V (100 μsec) |
| 1-B | 12.5 V (950 μsec) | 12.5 V (280 μsec) | 9.0 V (100 μsec) |
| 18-C | 9.5 V (1470 μsec) | 10 V (370 μsec) | 8.5 V (105 μsec) |

|  | Tilt angle (25° C.) | |
|---|---|---|
| Comp. | Initial (no electric field) | Under AC appln. (60 KHz, ±8 V, rectangular) |
| 1-A | 7.9 degrees | 8.2 degrees |
| 1-B | 7.5 degrees | 7.7 degrees |
| 18-C | 8.5 degrees | 13.0 degrees |

As apparent from Example 18 and Comparative Example 18, the liquid crystal composition 18-B obtained by mixing mesomorphic compounds having a negative dielectric anisotropy with the liquid crystal composition 1-B according to the present invention provided a wider driving margin and also provided a remarkably improved display characteristic when used in a display method utilizing AC application (or AC stabilization).

For example, the dielectric anisotropy Δε of a mesomorphic compound or a liquid crystal composition referred to herein may be measured in the following manner.

A 5 micron-thick homogeneous alignment cell having an electrode of 0.7 cm$^2$ in area and a homogeneous alignment layer (rubbed polyimide) on both substrates, and a 5 micron-thick homeotropic alignment cell having an electrode of 0.7 cm$^2$ in area and a homeotropic alignment layer (aligning agent: "ODS-E" available As described hereinabove, the ferroelectric liquid crystal composition according to the present invention provides a liquid crystal device which shows a good switching characteristic, a wide driving voltage margin and a wide temperature margin so that the device shows an excellent performance of retaining good images in resistance to changes in environmental temperature and cell gap. Further, the liquid crystal composition according to the present invention further containing a mesomorphic compound having a negative dielectric anisotropy, provides a liquid crystal device which retains the above-mentioned characteristics and further shows a remarkably improved display characteristic when used in a driving method utilizing AC stabilization.

What is claimed is:

1. A ferroelectric chiral smectic liquid crystal composition, comprising:

at least one compound represented by the following formula (I):

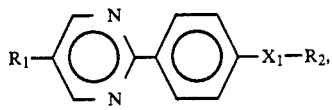
(I)

wherein $R_1$ may be optically active and denotes a linear or branched alkyl group having 1-18 carbon atoms denotes a linear alkyl group, wherein the sum of carbon atoms shown by the substituent —$(CH_2)_n$—$CH(CH_3)R_2$ is 5 to 18; $R_2$ and $X_1$ denotes a single bond, —O—,

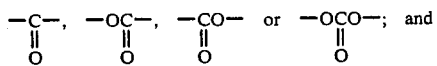; and at least one compound represented by the following formula (II):

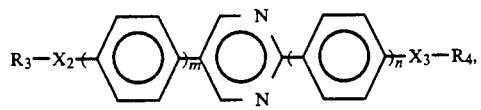
(II)

wherein $R_3$ and $R_4$ denote a linear or branched alkyl group having 1-18 carbon atoms; $X_2$ and $X_3$ denote a single bond, —O—,

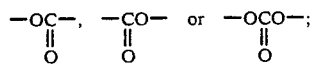;

and m and n are 0, 1 or 2 with proviso that m+n=2 or more.

2. A composition according to claim 1, which further comprises a mesomorphic compound having a negative dielectric anisotropy.

3. A composition according to claim 2, wherein said mesomorphic compound has a dielectric anisotropy $\Delta\epsilon$ of below −2.

4. A composition according to claim 3, wherein said mesomorphic compound has a dielectric anisotropy $\Delta\epsilon$ of below −5.

5. A composition according to claim 4, wherein said mesomorphic compound has a dielectric anisotropy $\Delta\epsilon$ of below −10.

6. A composition according to claim 2, wherein said mesomorphic compound having a negative dielectric anisotropy is a mesomorphic compound represented by any of the following formulae (III-1) to (III-5);

Formula(III-1):

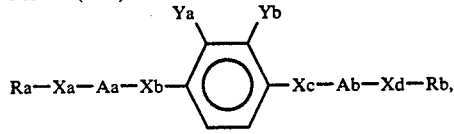

wherein Ra and Rb denote a linear or branched alkyl group capable of having a substituent; Xa and Xd denote a single bond, —O—,

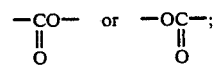

Xb and Xc denote a single bond,

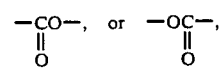

or —$CH_2CH_2$—; Aa and Ab denote a single bond,

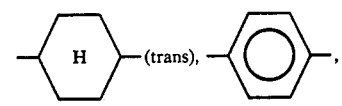

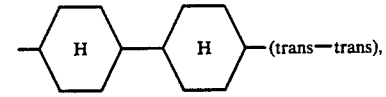

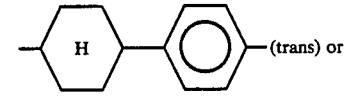

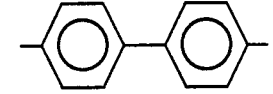

with proviso that when Aa and Ab are both single bonds, Xb and Xc are both single bonds, and Xa and Xd are both single bonds or —O—, or Xa is

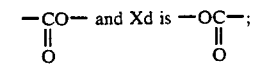

and Ya and Yb are cyano group, halogen or hydrogen with proviso that Ya and Yb cannot be hydrogen simultaneously;

Formula(III-2):

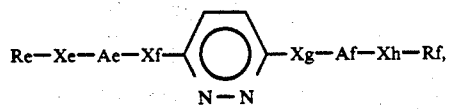

wherein Re and Rf denote a linear or branched alkyl group; Xe and Xh are a single bond, —O—,

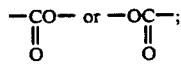

Xf and Xg are

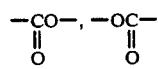

or a single bond; and Ae and Af are

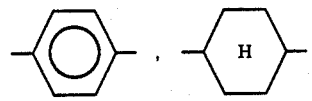

or a single bond with proviso that Ae and Af cannot be a single bond simultaneously;

Formula(III-3):

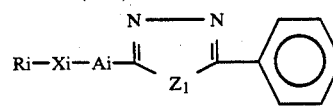

wherein Ai is a single bond or

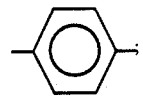

Aj is a single bond,

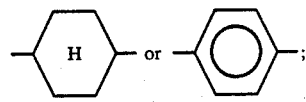

Ri and Rj are a linear or branched alkyl group substituent with proviso so Ri and Rj are linear alkyl groups when Aj is a single bond; $Z_1$ is —O— or —S—; Xi and Xk are a single bond, —O—,

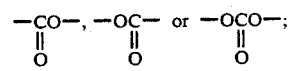

Xj is a single bond,

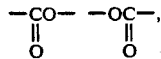

—CH$_2$O— or —OCH$_2$ with proviso that Xi is a single bond when Ai is a single bond, Xj is not a single bond when Aj is

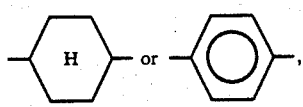

and Xk is a single bond when Aj is a single bond;

Formula (III-4):

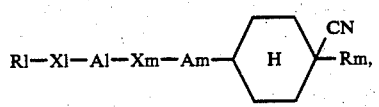

wherein Rl and Rm are a linear or branched alkyl group; Al and Am are a single bond,

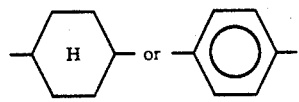

with proviso that Al and Am cannot be a single bond simultaneously; Xl is a single bond, —O—,

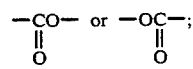

and Xm is a single bond

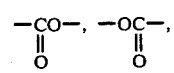

—CH$_2$O—, —OCH$_2$—, —CH$_2$CH$_2$— or —C≡C—;

Formula (III-5):

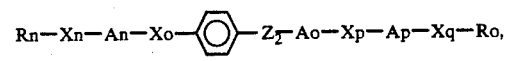

wherein Rn and Ro are a linear or branched alkyl group; Xn and Xq are a single bond, —O—,

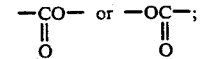

Xo and Xp are a single bond,

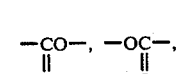

—CH$_2$O—, —OCH$_2$— or —CH$_2$CH$_2$—; An and Ap are a single bond,

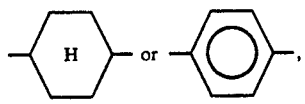
-continued
Ao is 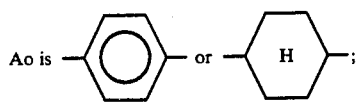 ;
and $Z_2$ is $-\underset{\underset{CN}{|}}{C}=CH-$ or $-\underset{\underset{CN}{|}}{CH}-CH_2-$.
7. A liquid crystal device, comprising a pair of electrode plates and a ferroelectric liquid crystal composition according to any one of claims 1-6 disposed between the electrode plates.
* * * * *

UNITED STATES PATENT AND TRADEMARK OFFICE
CERTIFICATE OF CORRECTION

PATENT NO. : 5,328,640
DATED : July 12, 1994
INVENTOR(S) : KENJI SHINJO, ET AL.

It is certified that error appears in the above-identified patent and that said Letters Patent is hereby corrected as shown below:

COLUMN 2

Line 8, "has" should read --have--.
Line 19, "U.S. Pat. No. 4367924," should read --U.S. Pat. No. 4,367,924,--.
Line 32, "electric" should read --electric field--.

COLUMN 3

Line 17, "duration At" should read --duration $\Delta$+--.
Line 52, "$|V_{s+vi}|$" should read --$|V_s+V_I|$--.

COLUMN 4

Line 19, "nonhelical" should read --non-helical--.

COLUMN 6

Line 67, "$\Delta\epsilon(2<|\Delta\epsilon\leq 10)$" should read --$\Delta\epsilon(2<|\Delta\epsilon|\leq 10)$--.

COLUMN 9

Line 63, "$X_3is$" should read --$X_3$ is--.

COLUMN 10

Line 3, "$X_3is$" should read --$X_3$ is--.
Line 19, "$R_3is$" should read --$R_3$ is--.

COLUMN 37

Form (3-48) "$C_5H_{11}$-n(3-48)" should read --$C_5H_{11}$-n--.

UNITED STATES PATENT AND TRADEMARK OFFICE
CERTIFICATE OF CORRECTION

PATENT NO. : 5,328,640
DATED : July 12, 1994
INVENTOR(S) : KENJI SHINJO, ET AL.

It is certified that error appears in the above-identified patent and that said Letters Patent is hereby corrected as shown below:

COLUMN 60

Line 19, "includes" should read --include--.

COLUMN 74

Line 28, "046/1985," should read --156046/1985,--.

COLUMN 78

Line 33,  "2-D  11.0 V     11.5 V     9.5 V"
              should read
--2-D  11.0 V        11.5 V        9.5 V
      (1100 μsec)  (300 μsec)  (100 μsec)--.

COLUMN 79

Line 39, "Voltage margin    12.5 V    12.5 V    9.0 V" should read --Voltage margin    12.5 V    13.0 V    9.5 V--.

COLUMN 95

Line 35, "$-X_1-R_2,$" should read -- $-X_1-CH_2)_n^*-CH(CH_3)-R_2,$ --.

Line 41, "atoms denotes" should read --atoms and $R_2$ denotes--.

Line 43, "$-CH(CH_3)R_2$" should read -- $-CH(CH_3)-R_2^*$ -- and "$R_2$" should read --n is an integer of 1-7;--.

Line 60, "atoms; $X_2$" should read --atoms wherein $R_3$ and $R_4$ are independently optionally substituted with alkoxy group; $X_2$--.

UNITED STATES PATENT AND TRADEMARK OFFICE
CERTIFICATE OF CORRECTION

PATENT NO. : 5,328,640
DATED : July 12, 1994
INVENTOR(S) : KENJI SHINJO, ET AL.

It is certified that error appears in the above-identified patent and that said Letters Patent is hereby corrected as shown below:

COLUMN 96

Line 26, "capable of having a substituent;" should read --wherein $R_6$ is optionally substituted with alkoxy group;--

Line 58, " 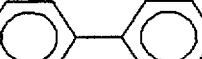 "

should read -- 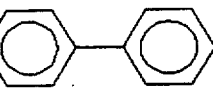 --.

COLUMN 97

Line 58, "substitu-" should read --wherein Ri is optionally substituted with Cl radical and Rj is optionally substituted with alkoxy group--.

Line 59, "ent" should be deleted and "so" should read --that--.

COLUMN 98

Line 40, "bond" should read --bond,--.

Signed and Sealed this

Twenty-first Day of March, 1995

Attest:

BRUCE LEHMAN

Attesting Officer     Commissioner of Patents and Trademarks